United States Patent
Sauer

(10) Patent No.: US 12,070,205 B2
(45) Date of Patent: Aug. 27, 2024

(54) SURGICAL SUTURING DEVICE FOR A REPLACEMENT ANATOMICAL STRUCTURE AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 580 days.

(21) Appl. No.: 17/400,339

(22) Filed: Aug. 12, 2021

(65) Prior Publication Data

US 2021/0369264 A1    Dec. 2, 2021

Related U.S. Application Data

(63) Continuation of application No. 14/247,688, filed on Apr. 8, 2014, now Pat. No. 11,116,496.

(51) Int. Cl.
*A61B 17/04* (2006.01)
*A61F 2/24* (2006.01)

(52) U.S. Cl.
CPC ...... *A61B 17/0469* (2013.01); *A61B 17/0482* (2013.01); *A61B 2017/0406* (2013.01); *A61B 17/0487* (2013.01); *A61F 2/2409* (2013.01)

(58) Field of Classification Search
CPC ...... A61F 2/24; A61F 2/2427; A61B 17/0469; A61B 17/0482; A61B 2017/0472; A61B 17/0483; A61B 2017/00663; A61B 2017/0406; A61B 17/0491; A61B 2017/0464; A61B 2017/0496; A61B 17/0057; A61B 17/0487; A61B 17/06004; A61B 17/0625
See application file for complete search history.

(56) References Cited

U.S. PATENT DOCUMENTS

| | | | |
|---|---|---|---|
| 5,431,666 A | 7/1995 | Sauer |
| 5,562,686 A | 10/1996 | Sauer |
| 5,766,183 A | 6/1998 | Sauer |
| 5,814,097 A | 9/1998 | Sterman |
| 5,860,992 A | 1/1999 | Daniel |
| 5,972,004 A | 10/1999 | Williamson |
| 6,368,334 B1 | 4/2002 | Sauer |
| 6,506,197 B1 | 1/2003 | Rollero |

(Continued)

FOREIGN PATENT DOCUMENTS

WO    WO2009137766    11/2009

OTHER PUBLICATIONS

Foreign Search Report; Mar. 1, 2018; ERBEL, Stephan; Extended European Search Report for EP15775923.

*Primary Examiner* — Katherine M Shi
(74) *Attorney, Agent, or Firm* — Michael E. Coyne

(57) ABSTRACT

A surgical suturing device has a guide tip defining cuff receiving and tissue bite areas. The guide tip has at least one needle guide configured to guide at least one needle through the cuff receiving area and the tissue bite area. Another surgical suturing device has a guide tip defining cuff receiving and tissue bite areas. The guide tip has at least one pair of needle guides configured to guide both the needles of at least one pair of needles through the cuff receiving area and the tissue bite area. The guide tip also has at least one pair of ferrule receiving apertures. The cuff receiving area and the tissue bite area are oriented to avoid cross-over of a suture passed by the at least one pair of needles through tissue in the tissue bite area and a replacement anatomical device sewing cuff in the cuff receiving area.

21 Claims, 18 Drawing Sheets

(56) References Cited

U.S. PATENT DOCUMENTS

| | | |
|---|---|---|
| 6,533,796 B1 | 3/2003 | Sauer |
| 6,641,592 B1 | 11/2003 | Sauer |
| 6,997,931 B2 | 2/2006 | Sauer |
| 7,211,093 B2 | 5/2007 | Sauer |
| 7,407,505 B2 | 8/2008 | Sauer |
| 7,731,727 B2 | 6/2010 | Sauer |
| 7,887,552 B2 | 2/2011 | Bachman |
| 8,313,496 B2 | 11/2012 | Sauer |
| 8,398,657 B2 | 3/2013 | Sauer |
| 8,652,149 B2 | 2/2014 | Sauer |
| 8,663,249 B2 | 3/2014 | Badhwar |
| 2002/0068949 A1 | 6/2002 | Williamson |
| 2005/0154402 A1 | 7/2005 | Sauer et al. |
| 2006/0253126 A1 | 11/2006 | Bjerken |
| 2007/0255296 A1 | 11/2007 | Sauer |
| 2009/0222027 A1 | 9/2009 | Sauer |
| 2011/0093063 A1 | 4/2011 | Schreck |
| 2011/0118758 A1 | 5/2011 | Sauer |
| 2011/0301701 A1 | 12/2011 | Padala |
| 2012/0016383 A1 | 1/2012 | Sauer |

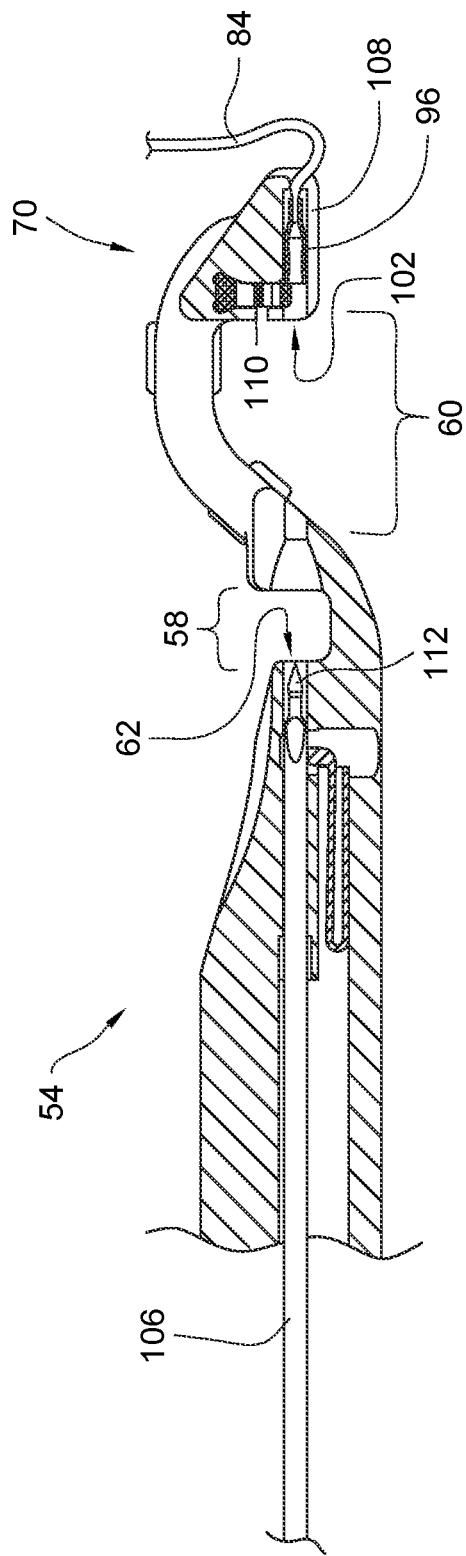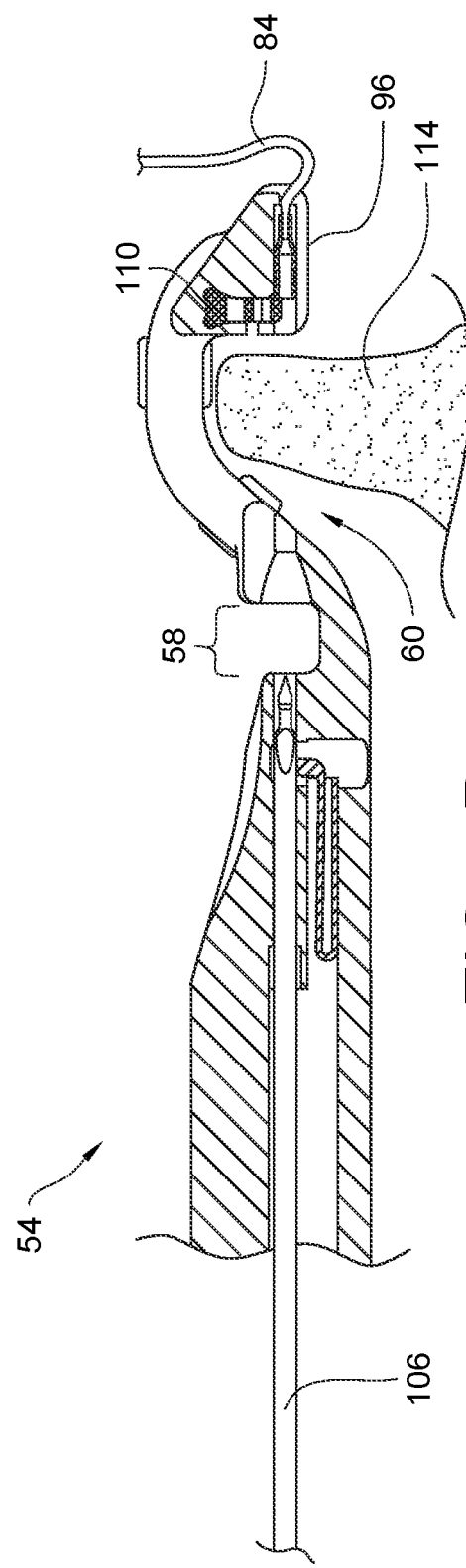

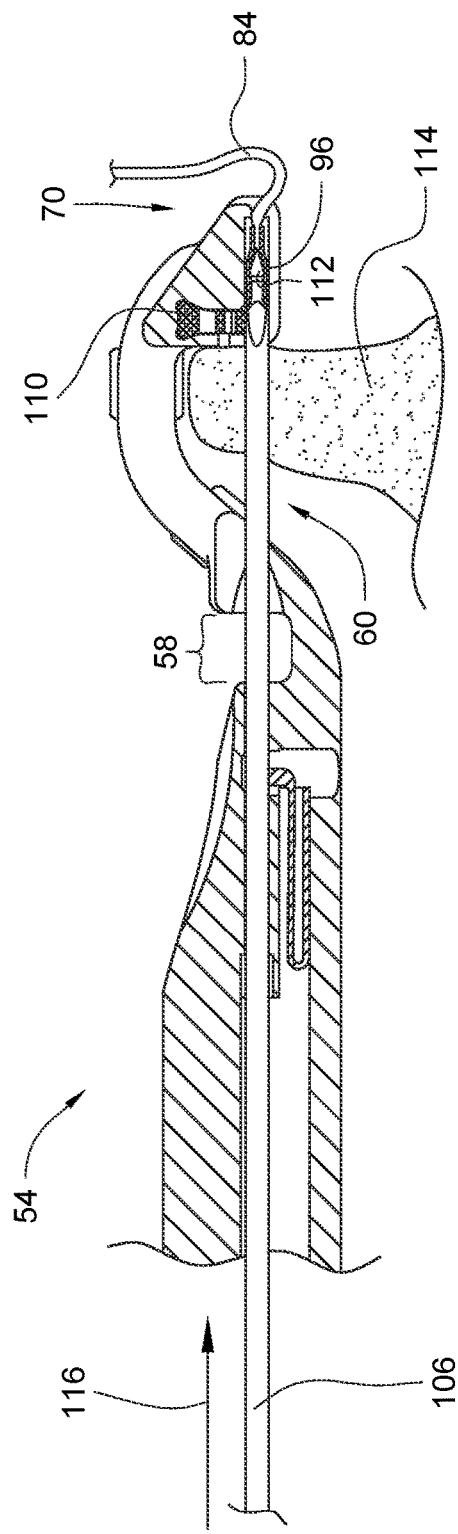
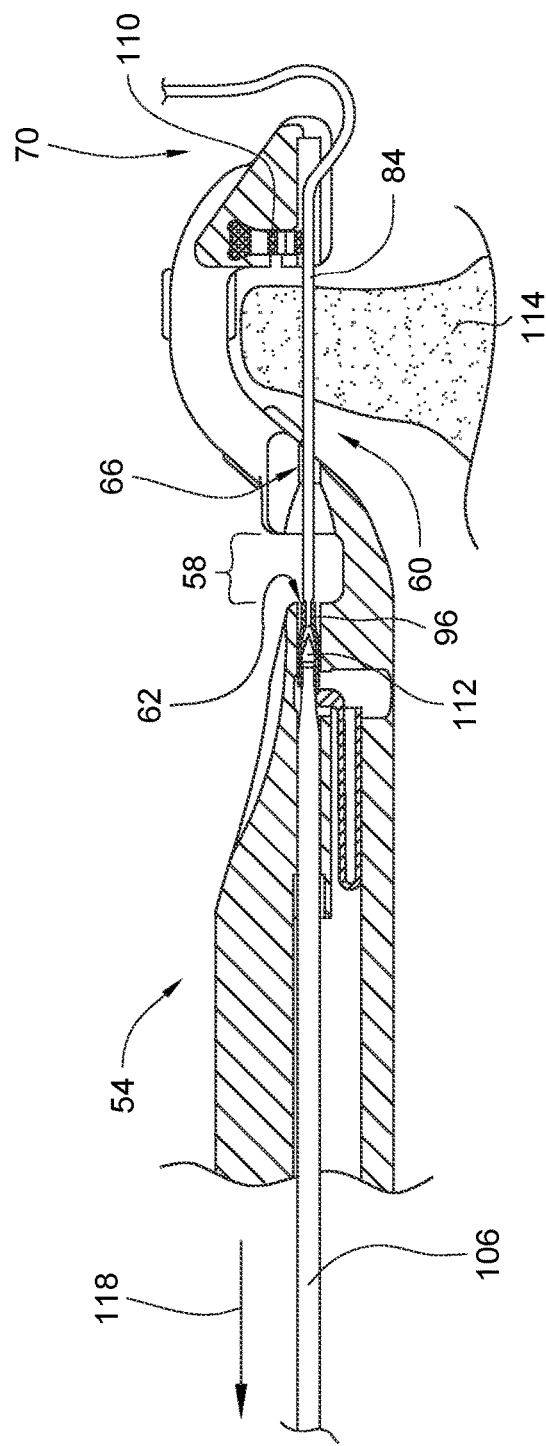

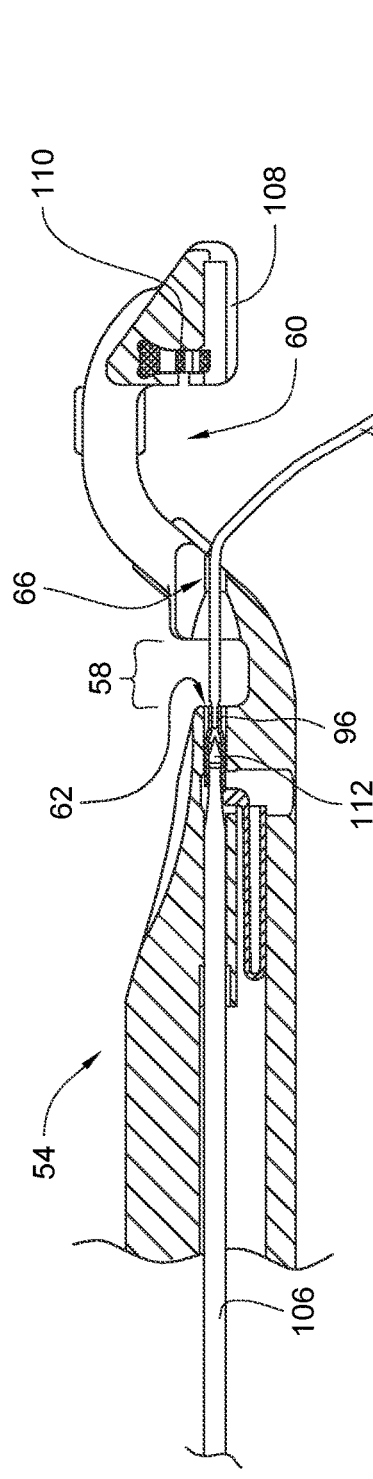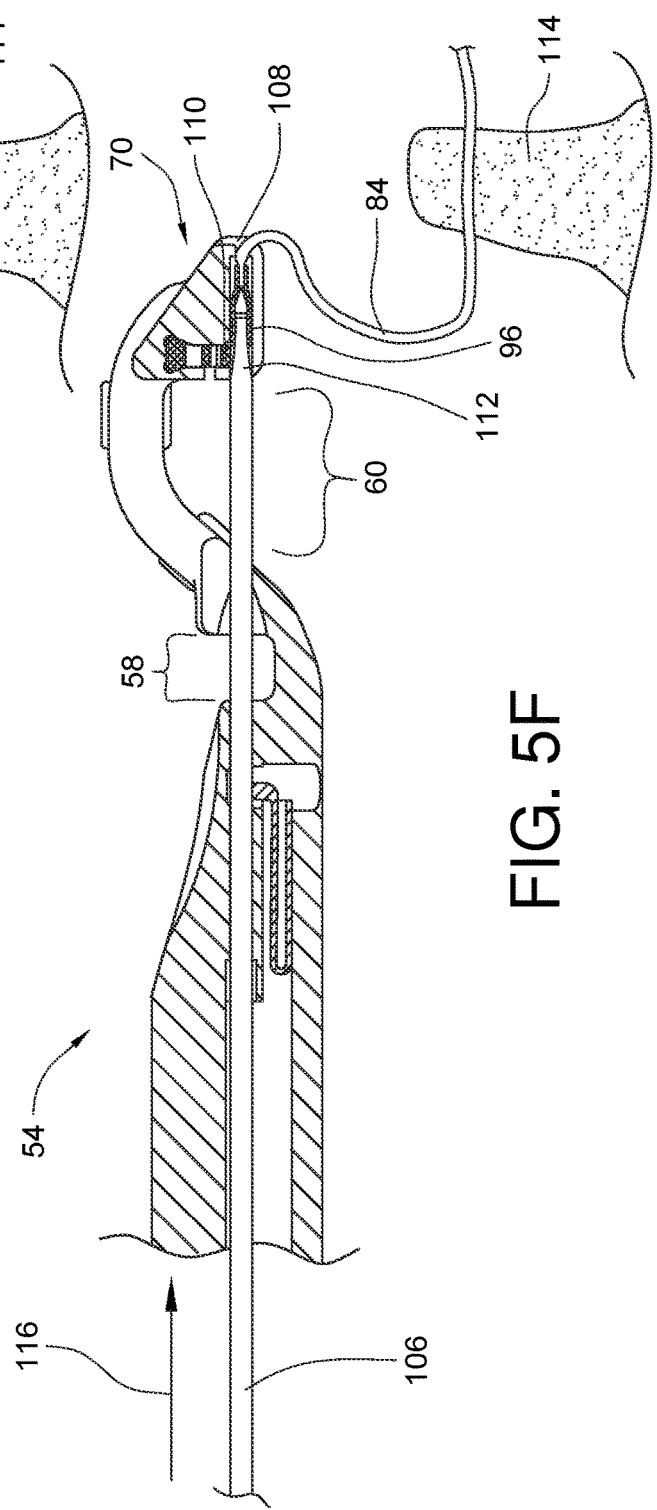
FIG. 5E
FIG. 5F

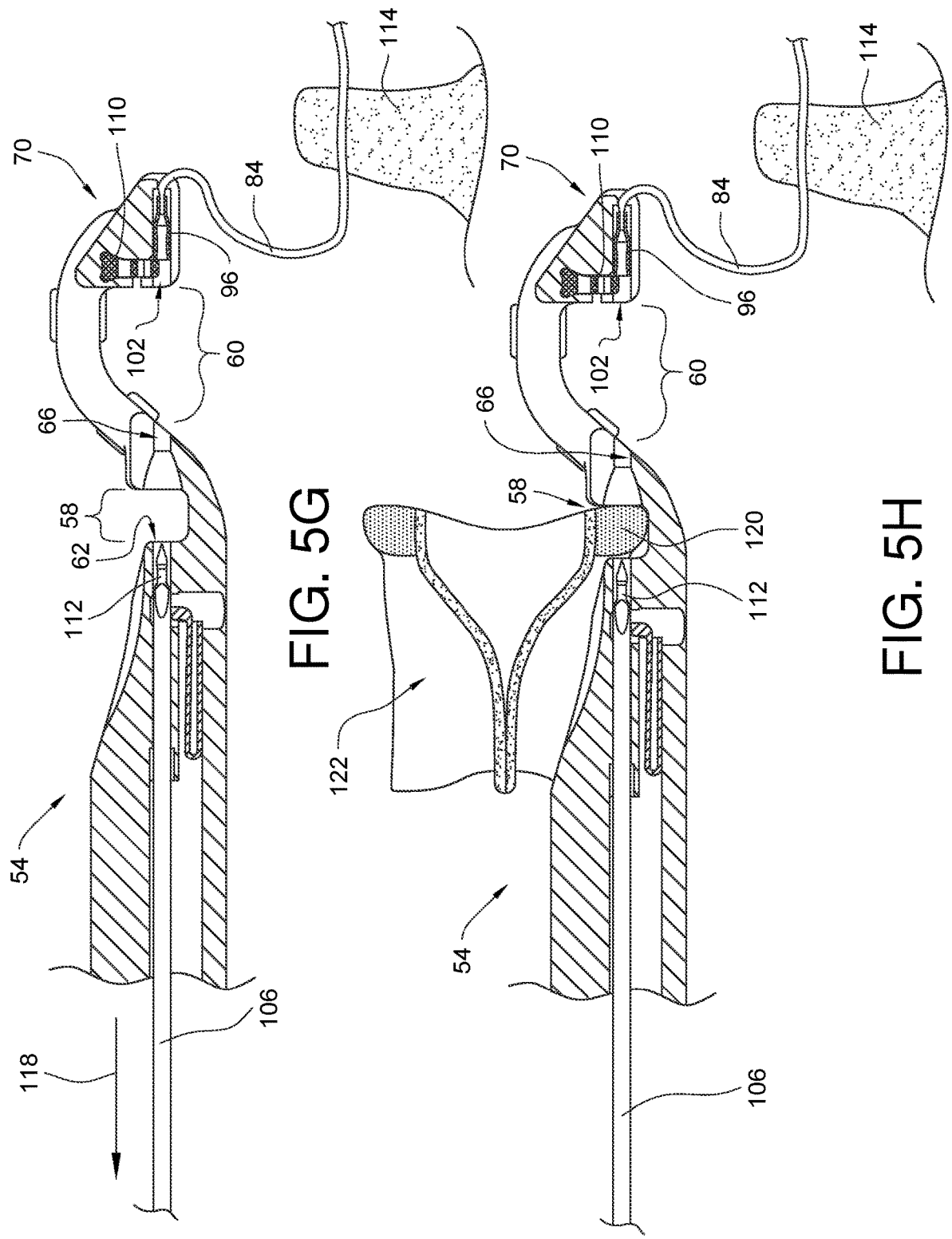

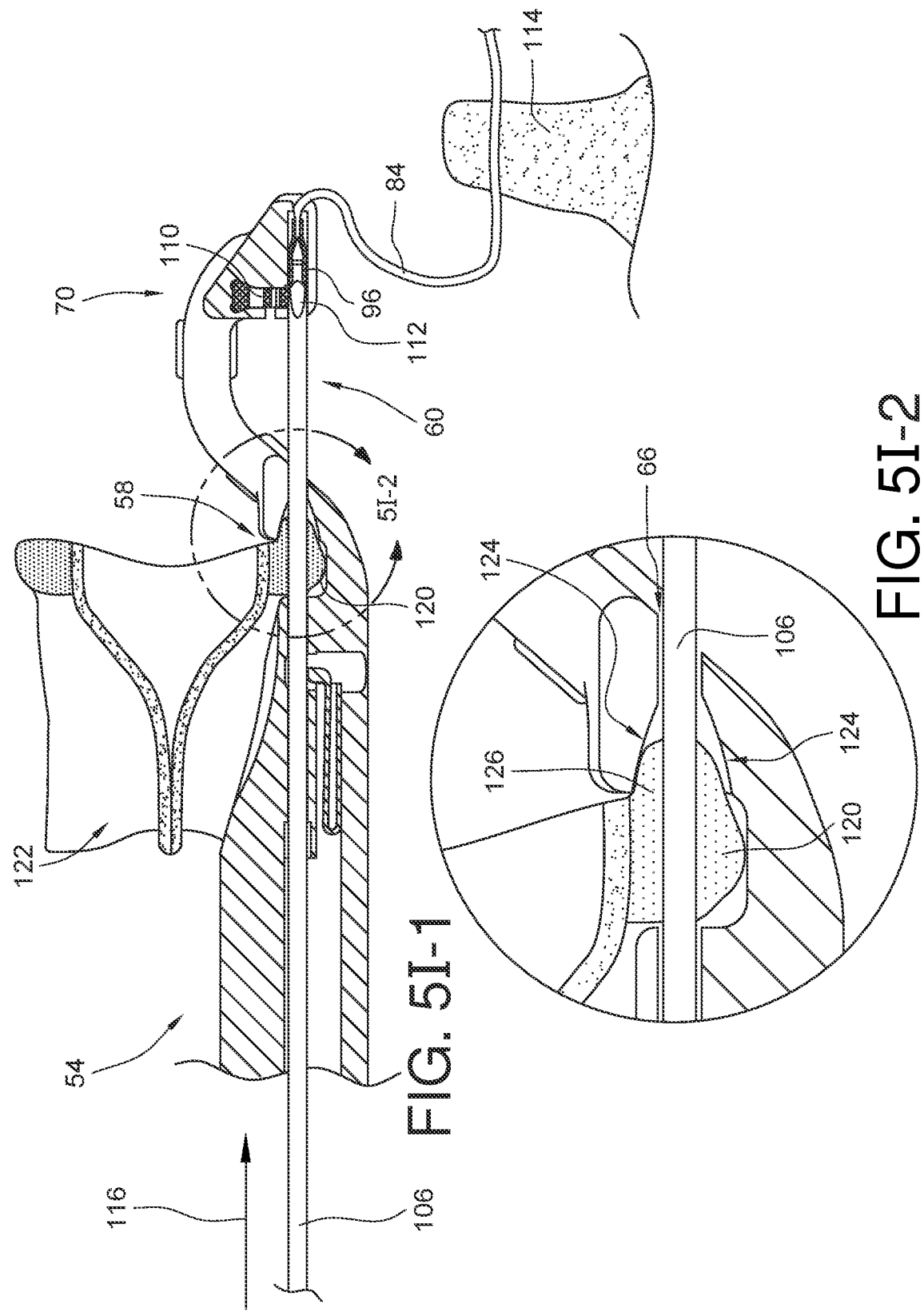

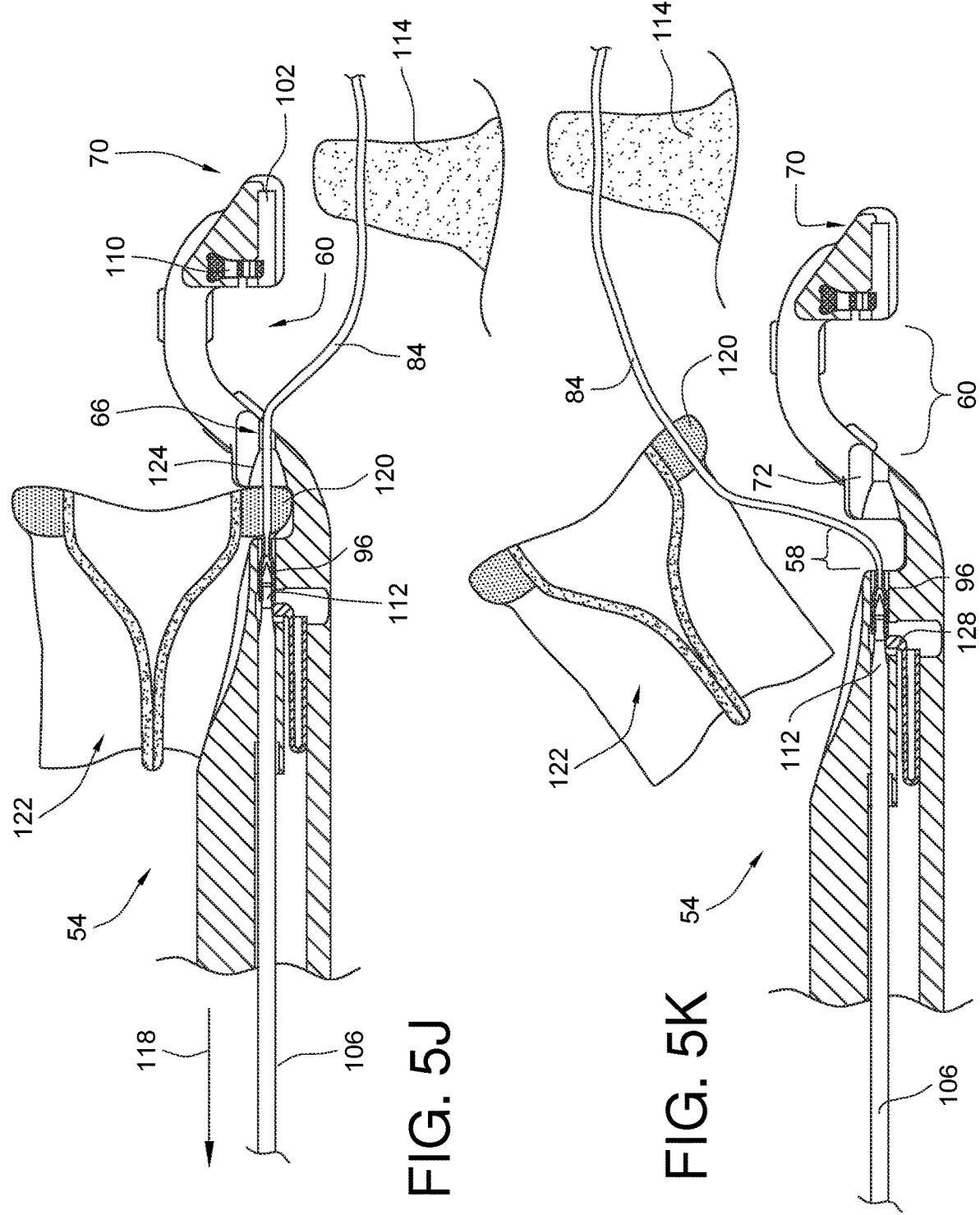

146 — USING FIRST AND SECOND NEEDLES, GUIDED AT LEAST IN PART BY A GUIDE TIP, THE NEEDLES EACH HAVING A FERRULE ENGAGING POINT REMOVABLY COUPLED TO RESPECTIVE FIRST AND SECOND FERRULES ON RESPECTIVE FIRST AND SECOND ENDS OF A SUTURE, MOVE THE FIRST AND SECOND SUTURE ENDS THROUGH A TISSUE BITE AREA AND A CUFF RECEIVING AREA, BOTH AREAS DEFINED BY A GUIDE TIP, SUCH THAT THE FIRST AND SECOND SUTURE ENDS PASS THROUGH TISSUE IN THE TISSUE BITE AREA WHILE THE CUFF RECEIVING AREA IS NOT ALIGNED WITH A SUTURE CUFF OF THE REPLACEMENT ANATOMICAL STRUCTURE

148 — USING THE FIRST AND SECOND NEEDLES, MOVE THE FIRST AND SECOND SUTURE ENDS THROUGH THE TISSUE BITE AREA AND THE CUFF RECEIVING AREA SUCH THAT THE FIRST AND SECOND SUTURE ENDS PASS THROUGH THE SUTURE CUFF OF THE REPLACEMENT ANATOMICAL STRUCTURE IN THE CUFF RECEIVING AREA WHILE THE TISSUE BITE AREA IS NOT ALIGNED WITH THE TISSUE

FIG. 8

SURGICAL SUTURING DEVICE FOR A REPLACEMENT ANATOMICAL STRUCTURE AND METHODS THEREOF

CROSS-REFERENCE TO RELATED APPLICATIONS

This patent application is a continuation of U.S. patent application Ser. No. 14/247,688, filed on Apr. 8, 2014 and entitled "SURGICAL SUTURING DEVICE FOR A REPLACEMENT ANATOMICAL STRUCTURE AND METHODS THEREOF," which is incorporated by reference herein in its entirety.

FIELD

The claimed invention relates to surgical suturing devices, and more specifically to a surgical suturing device for a replacement anatomical structure such as, but not limited to, a replacement heart valve.

BACKGROUND

The human heart relies on a series of one-way valves to help control the flow of blood through the chambers of the heart. For example, referring to FIG. 1, deoxygenated blood returns to the heart 20, via the superior vena cava 22 and the inferior vena cava 24, entering the right atrium 26. The heart muscle tissue contracts in a rhythmic, coordinated heartbeat, first with an atrial contraction which aids blood in the right atrium 26 to pass through the tricuspid valve 28 and into the right ventricle 30. Following atrial contraction, ventricular contraction occurs and the tricuspid valve 28 closes. Ventricular contraction is stronger than atrial contraction, assisting blood flow through the pulmonic valve 32, out of the heart 20 via the pulmonary artery 34, and to the lungs (not shown) for oxygenation. Following the ventricular contraction, the pulmonic valve 32 closes, preventing the backwards flow of blood from the pulmonary artery 34 into the heart 20.

Oxygenated blood returns to the heart 20, via the pulmonary veins 36, entering the left atrium 38. Left atrial contraction assists blood in the left atrium 38 to pass through the mitral valve 40 and into the left ventricle 42. Following the atrial contraction, ensuing ventricular contraction causes mitral valve 40 closure, and pushes oxygenated blood from the left ventricle 42 through the aortic valve 44 and into the aorta 46 where it then circulates throughout the body. Following left ventricular contraction, the aortic valve 44 closes, preventing the backwards flow of blood from the aorta 46 into the heart 20.

Unfortunately, one or more of a person's heart valves 28, 32, 40, and 44 can have or develop problems which adversely affect their function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve 40 prolapses (extends back) into the left atrium 38 during a ventricular contraction. Stenosis, by contrast, is when a heart valve does not fully patent due to stiff or fused leaflets, blood flow tract narrowing, or obstructive material buildup (e.g., calcium). The resultant narrowed outflow causes the heart to work harder to pump blood through it, possibly leading to heart failure.

Fortunately, advances in cardiac surgery, and in particular the evolution of reliable cardio-pulmonary bypass (CPB), have enabled open heart and less-invasive methods for heart valve replacement. During CPB, deoxygenated blood is diverted from the superior vena cava 22 and inferior vena cava 24 in or near the right atrium 26 of the heart 20, brought outside the body to a CPB machine, reoxygenated, and returned to the body at the aorta 46, or other great arterial vessels, thereby bypassing the heart 20 and making it possible to stop the heart 20 for cardiac surgery.

Unfortunately, while such cardiac procedures have become common-place, they are not without risks. In particular, extended time on a CPB machine can increase a patient's chances of developing complications involving the inflammatory system, heart, lungs, kidneys, brain, etc. An inflammatory response can be triggered by blood coming into contact with the foreign substances of the tubing leading to the CPB machine and the components of the machine itself. These types of inflammatory responses can damage the endothelium (inner layer of cells) of blood vessels, making them more susceptible to platelet and clot adhesion, and ultimately to an increased chance of atherosclerosis and other cardiovascular complications. Additionally, aortic clamping, necessary to establish the CPB, may cause inadequate blood flow to certain organs, for example, the heart, lungs, kidneys, or brain, thereby leading to possible ischemic damage to those organs. The risks of complications due to CPB increase dramatically with the amount of time a patient is actively connected to the CPB machine. Accordingly, surgeons rely on a combination of specialized skills, knowledge, technologies, and teamwork to operate as efficiently as possible in order to minimize a patient's time on CPB.

Depending on the number of valves being replaced for a patient, a typical heart valve replacement surgery can last between two to six hours, one to two hours of which can be spent on a CPB machine. While the patient is on CPB, the surgeon must gain access to the heart valve, remove the pathologic valve tissue as necessary, and install a replacement valve at the location of the original valve. The valve installation process, typically requiring suture placement and fastening, can be very time consuming, especially when surgeons are operating through small access sites when employing less-invasive techniques to reduce surgical trauma. Therefore, there is a need for devices and methods which enable surgeons to operate more efficiently during surgery to replace pathologic anatomical structures, such as, but not limited to, replacement heart valves. Such devices and methods can reduce the amount of time patients need to be attached to a CPB machine, thereby reducing the likelihood of CPB-related side effects. Faster cardiac operations offer additional benefits, such as reduced surgical team fatigue and more efficient use of critical resources. Expediting cardiac surgery can also improve patient outcomes.

SUMMARY

FIG. 1 is a cross-sectional view of a heart, illustrating the chambers and valves which function therein. A surgical suturing device is disclosed. The surgical suturing device has a guide tip defining a cuff receiving area and a tissue bite area. The guide tip has at least one needle guide configured to guide at least one needle through the cuff receiving area and the tissue bite area.

Another surgical suturing device is disclosed. The surgical suturing device has a shaft and at least one needle slideably coupled to the shaft. The surgical suturing device also has at least one actuator near a proximal end of the shaft and coupled to the at least one needle. The surgical suturing device further has a guide tip coupled to a distal end of the shaft. The guide tip defines a cuff receiving area and a tissue bite area. The guide tip also has at least one needle guide configured to guide the at least one needle through the cuff receiving area and the tissue bite area. The cuff receiver area and the tissue bite area face substantially opposite directions. The tissue bite area is closer than the cuff receiving area to a distal end of the guide tip. The at least one needle guide comprises a transition needle guide between the cuff receiving area and the tissue bite area. The transition needle guide comprises a flared end facing the cuff receiving area. The actuator is configured to move the at least one needle between a retracted position where the at least one needle is not passing through the cuff receiving area or the tissue bite area and an engaged position where the at least one needle is passing through the cuff receiving area and the tissue bite area and visa versa.

A further surgical suturing device is disclosed. The surgical suturing device has first and second needles, each having a ferrule engaging end. The surgical suturing device also has a guide tip defining a cuff receiving area and a tissue bite area. The guide tip has first and second ferrule receiving apertures. The guide tip also has a first needle guide configured to guide the first needle through the cuff receiving area and the tissue bite area. The guide tip further has a second needle guide configured to guide the second needle through the cuff receiving area and the tissue bite area. The guide tip also has a cuff support configured to align at least a portion of a sewing cuff for a replacement anatomical structure within the cuff receiving area. The cuff receiving area and the tissue bite area face substantially different directions. The tissue bite area is closer than the cuff receiving area to a distal end of the guide tip. The first and second needle guides comprise first and second transition needle guides, respectively, between the cuff receiving area and the tissue bite area. The first and second transition needle guides comprise first and second flared ends, respectively, facing the cuff receiving area.

Another surgical suturing device is disclosed. The surgical suturing device has a guide tip defining a cuff receiving area and a tissue bite area. The guide tip has at least one pair of needle guides configured to guide both the needles of at least one pair of needles through the cuff receiving area and the tissue bite area. The guide tip also has at least one pair of ferrule receiving apertures. The cuff receiving area and the tissue bite area are oriented to avoid cross-over of a suture passed by the at least one pair of needles through tissue in the tissue bite area and a replacement anatomical device sewing cuff in the cuff receiving area.

A method of installing a replacement anatomical structure is disclosed. Using at least one needle guided at least in part by a guide tip, at least one suture end is moved through a tissue bite area and a cuff receiving area, both areas defined by the guide tip, such that the at least one suture end passes through tissue in the tissue bite area while the cuff receiving area is not aligned with a sewing cuff of the replacement anatomical structure. Using the at least one needle guided at least in part by the guide tip, at least one suture end is moved through the tissue bite area and the cuff receiving area such that the at least one suture end passes through the sewing cuff of the replacement anatomical structure in the cuff receiving area while the tissue bite area is not aligned with the tissue.

Another method of installing a replacement anatomical structure is disclosed. Using first and second needles, guided at least in part by a guide tip, the needles each having a ferrule engaging end removably coupled to respective first and second ferrules on respective first and second ends of a suture, the first and second suture ends are moved through a tissue bite area and a cuff receiving area, both areas defined by a guide tip, such that the first and second suture ends pass through tissue in the tissue bite area while the cuff receiving area is not aligned with a sewing cuff of the replacement anatomical structure. Using the first and second needles, the first and second suture ends are moved through the tissue bite area and the cuff receiving area such that the first and second suture ends pass through the sewing cuff of the replacement anatomical structure in the cuff receiving area while the tissue bite area is not aligned with the tissue.

BRIEF DESCRIPTION OF THE DRAWINGS

FIG. 5A is a partial cross-sectional view of one embodiment of a surgical suturing device having a guide tip defining a cuff receiving area and a tissue bite area. The guide tip also has at least one needle guide configured to guide at least one needle through the cuff receiving area and the tissue bite area.

FIG. 5B is a partial cross-sectional view of the surgical suturing device of FIG. 5A wherein the tissue bite area is being placed over a portion of tissue.

FIG. 5C is a partial cross-sectional view of the surgical suturing device of FIG. 5A wherein the needle is being guided through the tissue in the tissue bite area.

FIG. 5D is a partial cross-sectional view of the surgical suturing device of FIG. 5A wherein a ferrule coupled to a suture is being drawn back through the tissue in the tissue bite area by the needle.

FIG. 5E is a partial cross-sectional view of the surgical suturing device of FIG. 5A wherein the tissue bite area is lifted off of the tissue having the suture passed therethrough.

FIG. 5F is a partial cross-sectional view of the surgical suturing device of FIG. 5A wherein the ferrule coupled to the suture is returned by the needle to a distal end of the guide tip.

FIG. 5G is a partial cross-sectional view of the surgical suturing device of FIG. 5A wherein the needle is returned to a proximal end of the guide tip.

FIG. 5H is a partial cross-sectional view of the surgical suturing device of FIG. 5A wherein a sewing cuff of a replacement valve has been placed in the cuff receiving area of the guide tip.

FIG. 5I-1 is a partial cross-sectional view of the surgical suturing device of FIG. 5A wherein the needle is being guided through the sewing cuff in the cuff receiving area.

FIG. 5I-2 is an enlarged view of a portion of FIG. 5I-1 highlighting one embodiment of a flared end of the needle guide facing the cuff receiving area.

FIG. 5J is a partial cross-sectional view of the surgical suturing device of FIG. 5A wherein the ferrule coupled to the suture is being drawn back through the sewing cuff in the cuff receiving area by the needle.

FIG. 5K is a partial cross-sectional view of the surgical suturing device of FIG. 5A wherein the sewing cuff having the suture passed therethrough is removed from the cuff receiving area.

FIGS. 7 and 8 illustrate different embodiments of methods for installing a replacement anatomical structure.

Figure 1:
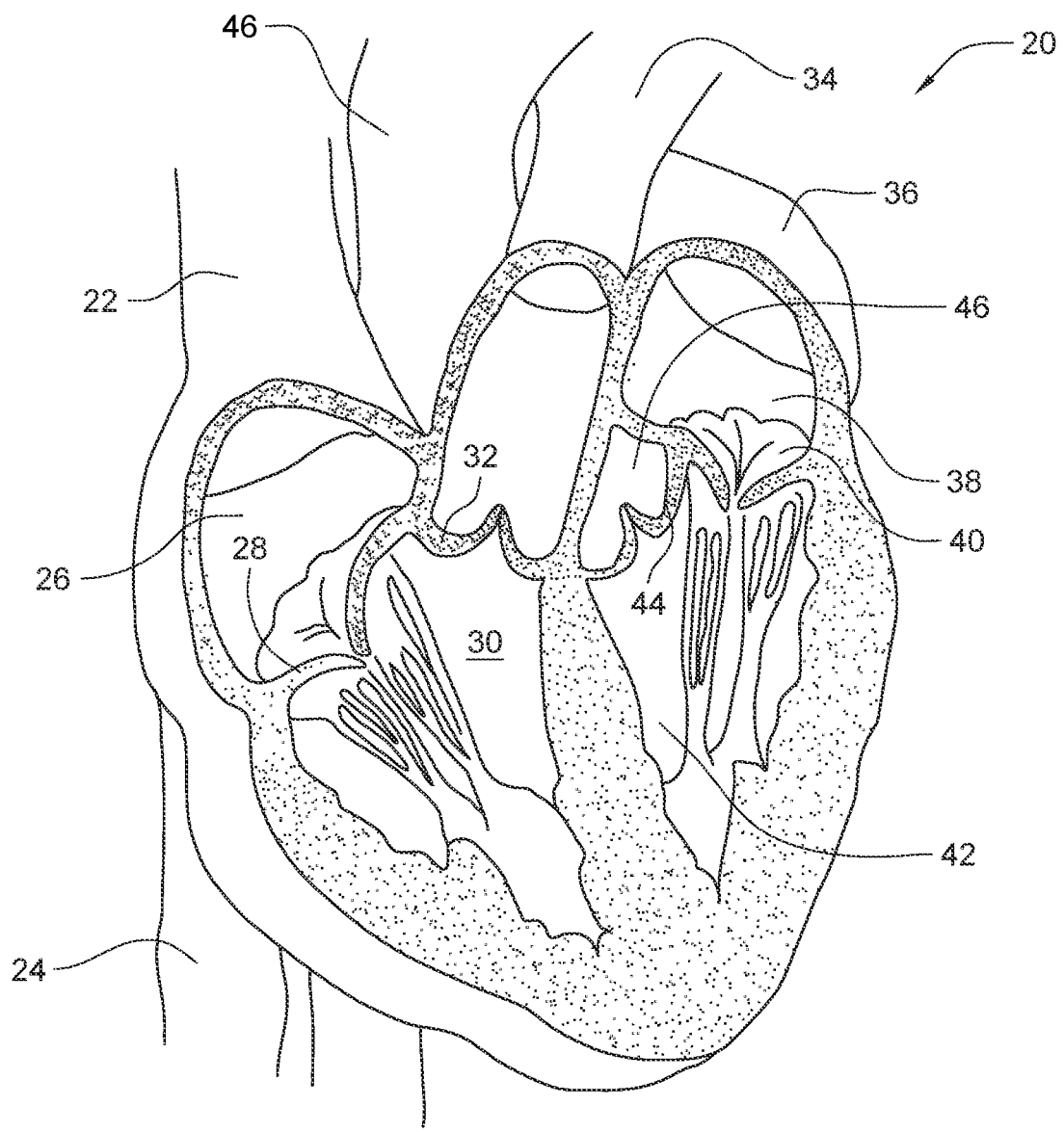
FIG. 1 is a cross-sectional view of a heart, illustrating the chambers and valves which function therein.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
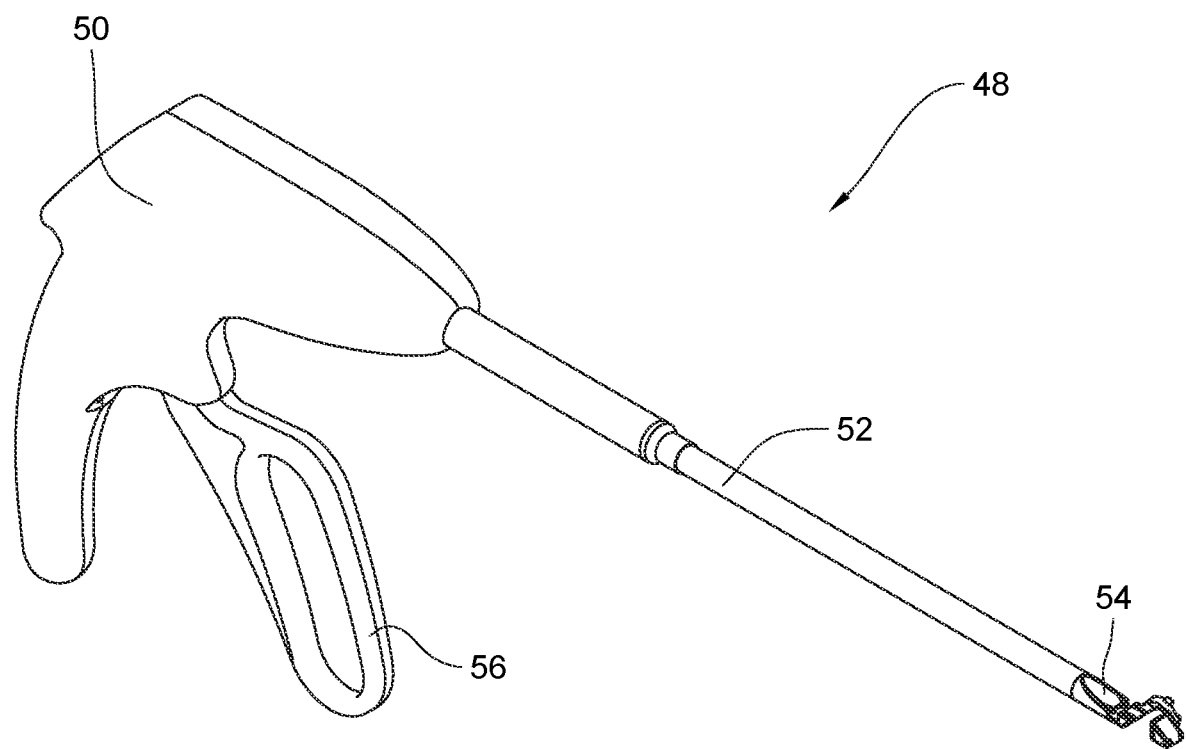
FIG. 2 is a perspective view of one embodiment of a surgical suturing device.

FIG. 2 is a perspective view of one embodiment of a surgical suturing device 48. The surgical suturing device 48 may have a housing 50 coupled to a shaft 52. A guide tip 54 is coupled to an end of the shaft 52, opposite from the housing 48. In some embodiments, the guide tip 54 may be continuous with the shaft 52, rather than a separate assembly piece which is coupled to the shaft 52. The surgical suturing device 48 also has a needle actuator 56 which is configured to move one or more needles within the guide tip 54 as will be described in greater detail below. Depending on the embodiment, some non-limiting examples of suitable shafts include a straight shaft (as illustrated), a curved shaft, a bent shaft, a flexible shaft, and an articulating shaft. Also depending on the embodiment, some non-limiting examples of suitable needle actuators include a handle (as illustrated), a lever, a knob, a slide, a gear, a wheel, a motor, and a solenoid.

Figure 3A:
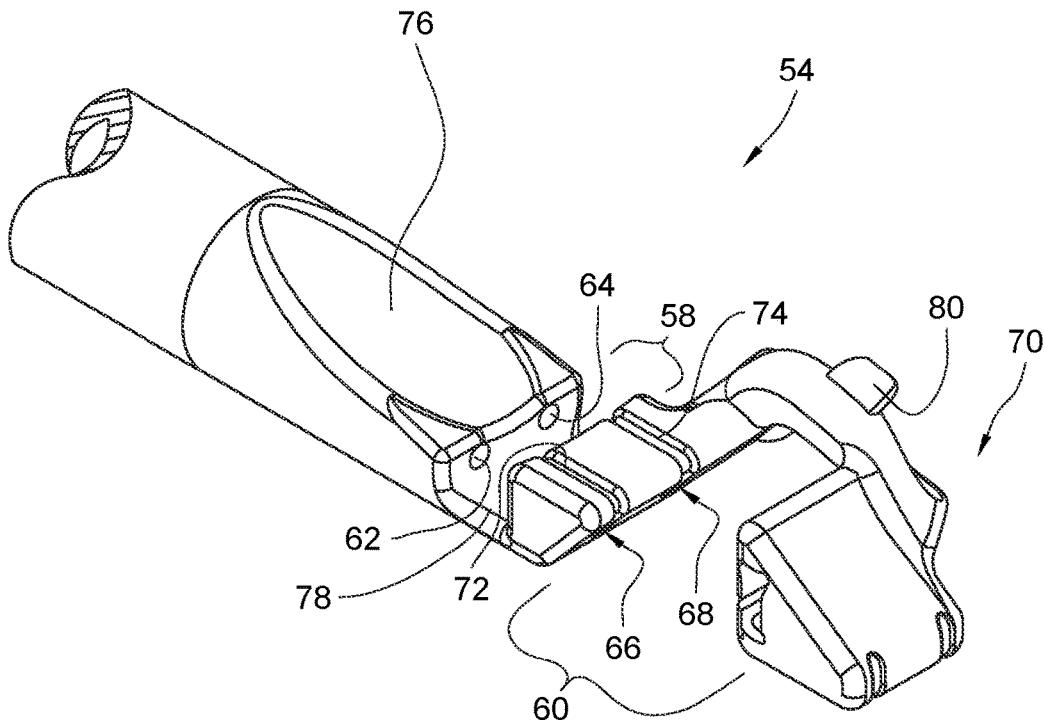
FIGS. 3A and 3B illustrate different perspective views of one embodiment of a guide tip for use in a surgical suturing device.
Figure 3B:
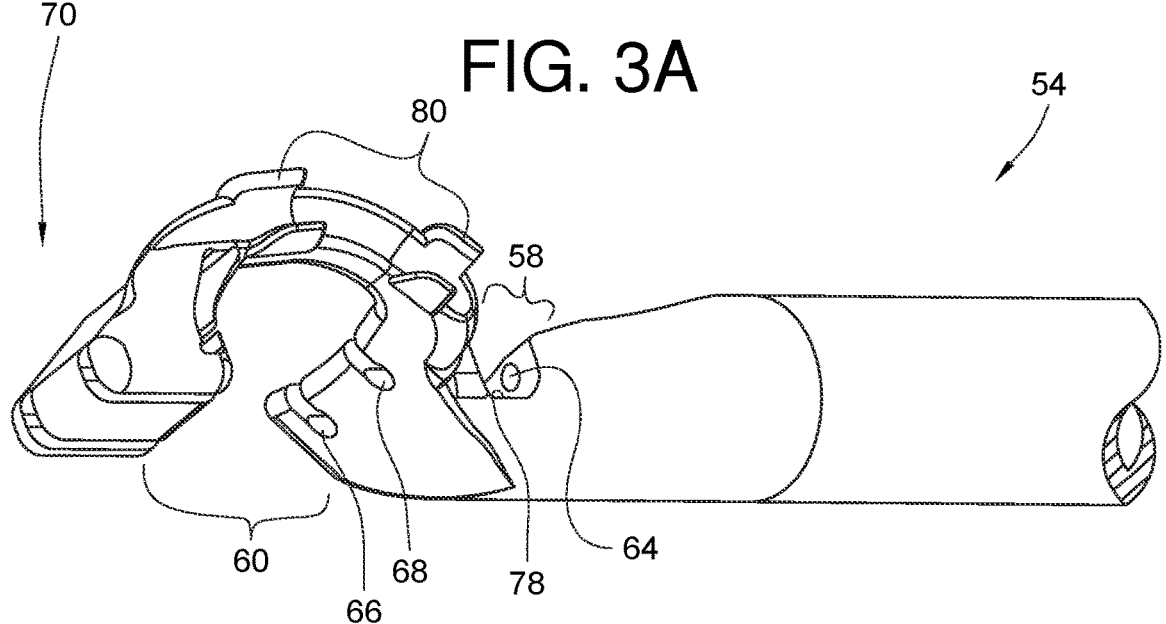

FIGS. 3A and 3B illustrate different perspective views of one embodiment of a guide tip 54 for use in a surgical suturing device. The guide tip 54 defines a cuff receiving area 58 and a tissue bite area 60. In this embodiment, the guide tip 54 has one needle guide 62 for a first needle (not shown in this view) and another needle guide 64 for a second needle (also not shown in this view). In this embodiment, the guide tip 54 also has first and second transition needle guides 66, 68 for the first and second needles, respectively, between the cuff receiving area 58 and the tissue bite area 60. The first and second needle guides 62, 64, and the first and second transition needle guides 66, 68 are configured to guide the needles through the cuff receiving area 58 and the tissue bite area 60.

Different embodiments may be configured to have differing numbers of needles. For example, some embodiments may only have a single needle, while other embodiments may have two or more needles. Accordingly, embodiments of the surgical suturing device should have at least one needle guide configured to guide at least one needle through the cuff receiving area 58 and the tissue bite area 60.

As will be discussed in more detail later in this specification, the tissue bite area 60 is sized to be placed around a portion of tissue where a replacement anatomical structure will be attached. Similarly, the cuff receiving area 58 is sized to receive a portion of a sewing cuff coupled to the replacement anatomical structure. A variety of replacement anatomical structures are contemplated in this specification. For simplicity, however, a replacement heart valve will be discussed herein as an exemplary instance of a replacement anatomical structure. Those skilled in the art, however, will readily see that the devices, methods, and equivalents of such devices and methods disclosed herein may readily be used with other replacement anatomical structures.

In the embodiments discussed herein, the cuff receiving area 58 and the tissue bite area 60 face substantially opposite directions. This opposite facing may advantageously help to prevent sutures from crossing over themselves in-between the sewing cuff of a replacement anatomical structure and the tissue where it is attached. Other embodiments, however, may have the cuff receiving area 58 and the tissue bite area 60 facing substantially similar directions. Further embodiments may have a cuff receiving area 58 and a tissue bite area 60 which face any possible combination of different directions.

In the embodiments illustrated herein, the tissue bite area 60 is closer than the cuff receiving area 58 to a distal end 70 of the guide tip 54. In other embodiments, however, the cuff receiving area 58 may be closer than the tissue bite area 60 to the distal end 70.

In the embodiment of FIG. 3A, the guide tip 54 further defines a first suture removal passage 72 for the first transition needle guide 66. Similarly, the guide tip 54 defines a second suture removal passage 74 for the second transition needle guide 68. The first and second suture removal passages 72, 74 each extend for the entire length of their respective transition needle guides 66, 68. The suture removal passages 72, 74 are each wide enough to allow passage of a suture therethrough, if desired, but preferably not wide enough to allow a needle being guided by a respective transition needle guide 66, 68 to pass therethrough. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

In cases where the replacement anatomical structure is a replacement heart valve, the valve may extend relative to the sewing cuff of the replacement anatomical structure such that it could interfere, in some instances, with the guide tip 54 when the sewing cuff is placed into the cuff receiving area 58. Therefore, in some embodiments, the guide tip 54 may include a valve clearance cutout 76 adjacent to the cuff receiving area 58 as illustrated by the non-limiting example shown in FIG. 3A.

The guide tip 54 may also include a cuff support 78 which is configured to align at least a portion of a sewing cuff (not shown in FIGS. 3A-3B) for a replacement anatomical structure within the cuff receiving area 58. Depending on the embodiment, the cuff support 78 may have a support contour which corresponds to at least a portion of a cuff contour of the sewing cuff.

Depending on the embodiment, the guide tip 54 may also be configured as a reloadable device, enabling the guide tip to be reloaded one or more times with a different suture. Some valve replacements may involve the placement of twenty or more sutures, so reloading capability can provide great value and potential time savings. As one example of a reloadable device configuration, in this embodiment, the guide tip 54 also has a reloadable suture delivery mechanism, such as, but not limited to, tube holder 80. The suture delivery tube holder 80 is configured to removably hold a suture delivery tube, such as the suture delivery tube 82 shown in FIG. 4A. The suture delivery tube 82 may be made from any flexible or non-flexible material suitable for use in surgical applications. As just one example, a suture delivery tube 82 may be loaded with a suture 84 such that a middle portion 86 of the suture 84 is at least partially held within the suture delivery tube 82. Part of the middle suture portion 86 may protrude from a first end 88 of the delivery tube 82. The two ends 90, 92 of the suture 84 may protrude from a second end 94 of the delivery tube 82. Each end 90, 92 may be coupled to a respective ferrule 96, 98. The ferrules 96, 98, and their function, will be discussed in more detail further in this specification. The suture ends 90, 92 may also pass through a pledget 100 in some embodiments. As will be shown later in this specification, the pledget 100 can provide support to a suture passing through tissue to help prevent a suture stitch from ripping through the tissue.

Figure 4A:
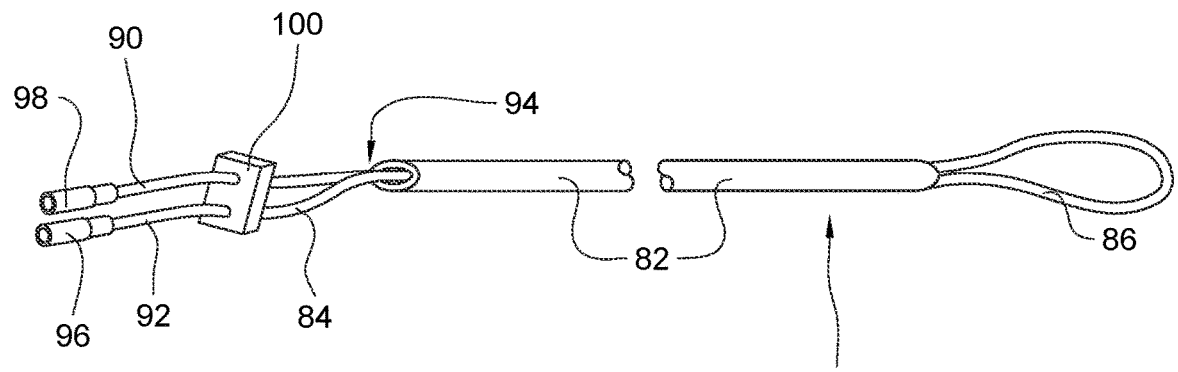
FIG. 4A illustrates one embodiment of a suture delivery tube for use with a guide tip of a surgical suturing device.
Figure 4B:
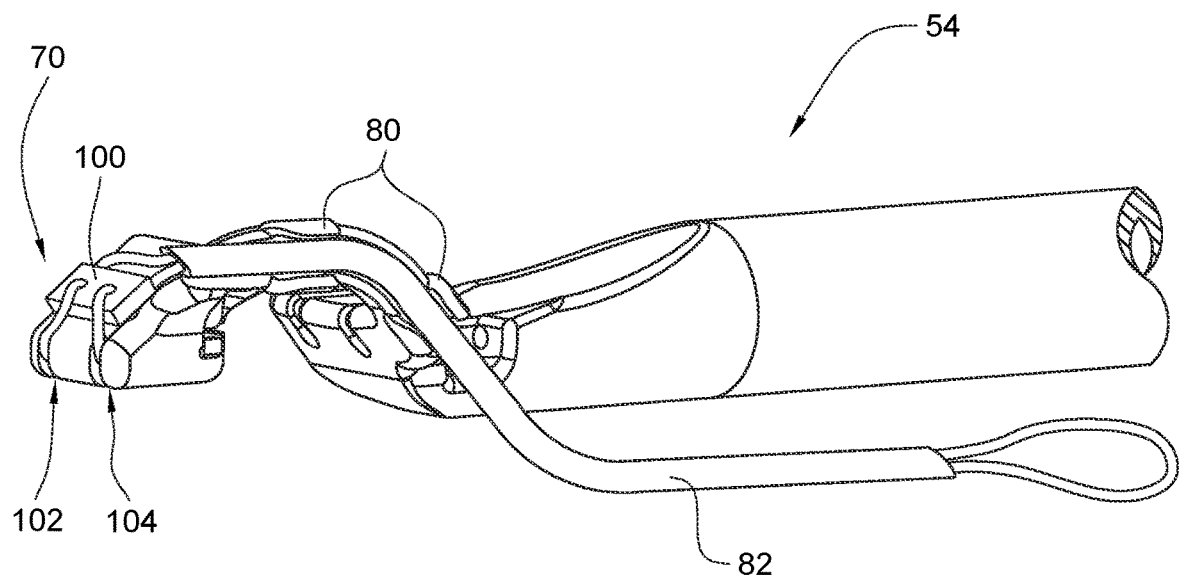
FIG. 4B illustrates the suture delivery tube of FIG. 4A removably held by the guide tip of FIG. 3B.

FIG. 4B illustrates the suture delivery tube 82 of FIG. 4A removably held by the guide tip 54 of FIG. 3B. The guide tip 54 has first and second ferrule receiving apertures 102, 104. The first and second ferrules 96, 98 (not visible in FIG. 4B) are loaded into the first and second ferrule receiving apertures 102, 104, respectively, and the suture delivery tube 82 is clipped into the delivery tube holder 80. If present, the pledget 100 can lie against the distal end 70 of the guide tip 54. The distal end 70 may advantageously be sized to receive the pledget 100 in this loaded configuration. After one suture has been used (as will be described later in this specification), the used suture delivery tube 82 may be removed and a new tube with suture reloaded into the guide tip 54.

FIGS. 5A-5K illustrate, in partial cross-sectional view, an example of using one embodiment of a surgical suturing device to install a replacement heart valve. As shown in FIG. 5A and discussed previously, the surgical suturing device has a guide tip 54. The guide tip 54 defines a cuff receiving area 58 and a tissue bite area 60. The guide tip 54 also has at least one needle guide 62 configured to guide at least one needle 106 through the cuff receiving area 58 and the tissue bite area 60. The distal end 70 of the guide tip 54 has at least one ferrule receiving aperture 102 that releasably holds a ferrule 96 coupled to a suture 84. The suture 84 may pass into or out of the ferrule receiving aperture 102 through an aperture suture slot 108 which extends for at least part of, and preferably for all of, the length of the ferrule receiving aperture 102. The ferrule 96 is held in the ferrule receiving aperture 102 by a latch 110. As will be described in more detail with regard to FIGS. 5B-5K, the needle 106 has an end 112 which can selectively be actuated to extend out to the ferrule receiving aperture 102, removably couple to the ferrule 96, and draw the ferrule 96 back through the tissue bite area 60 and the cuff receiving area 58. The needle 106 (and the ferrule 96 it is holding) may then be extended out to the ferrule receiving aperture 102 again to return the ferrule 96 to the ferrule receiving aperture 102. The needle 106 can then be retracted, leaving the ferrule 96 behind in the ferrule receiving aperture, and the process can be repeated. As one example, a suitable apparatus and method for accomplishing such needle movement and ferrule accompaniment is disclosed in U.S. Pat. No. 7,407,505 to Sauer, entitled, "Running Stitch Suturing Device", the entirety of which is hereby incorporated by reference. The ferrule 96 at the end of the suture 84 can be any structure or material which actively or passively works in conjunction with the needle 106 to enable coupling and decoupling of the needle 106 and the suture end in a manner similar to that described herein such that the suture end follows a similar path through the tissue and sewing cuff as will be described in the following sections.

In FIG. 5B, the tissue bite area 60 is placed over a portion of tissue 114 where it is desirable to attach a corresponding part of a replacement anatomical structure, such as, but not limited to a replacement heart valve. As one example, the tissue 114 could be a portion of an annulus from which defective valve leaflets have been removed.

In FIG. 5C, the needle 106 has been advanced by an actuator (not shown) along a direction 116 parallel to a longitudinal axis of the needle 106 towards the distal end 70 of the guide tip 54. Along the way, the needle 106 is guided through the cuff receiving area 58 and the tissue bite area 60. Since there is tissue 114 in the tissue bite area 60, the needle 106 passes through the tissue 114. The needle 106 then enters the ferrule receiving aperture 102, passes by the latch 110, and couples to the ferrule 96.

In FIG. 5D, the needle 106 has been retracted by the actuator (not shown) along a direction 118 parallel to the longitudinal axis of the needle 106 away from the distal end 70 of the guide tip 54. The end 112 of the needle 106 starts out oriented as shown in FIG. 5C, and is configured in that orientation to provide no edge for the latch 110 to grab the ferrule 96, thereby enabling the needle 106 to withdraw the ferrule 96 (and the suture 84 attached to the ferrule 96) back through the tissue 114 in the tissue bite area 60, through the transition guide 66, back through the cuff receiving area 58, and back into the needle guide 62 as shown in FIG. 5D. The end 112 of the needle 106 (and usually the needle 106 with it) also rotates ninety degrees about the needle's longitudinal axis during the retraction in order to present a sloped side of the needle 106 for ferrule removal from the needle to be described in later steps. This method of ferrule removal is known to those skilled in the art and is disclosed, for example, in U.S. Pat. No. 7,407,505, which has already been incorporated herein by reference. The needle 106, as illustrated in FIG. 5D, depicts the needle after the needle rotation.

As illustrated in FIG. 5E, the tissue bite area 60 is then lifted off of the tissue 114. The suture 84 is free to pass through the aperture suture slot 108. As illustrated in FIG. 5F, the needle 106 (the end 112 of which is temporarily coupled to the suture ferrule 96) has been advanced again by an actuator along a direction 116 parallel to a longitudinal axis of the needle 106 towards the distal end 70 of the guide tip 54. Along the way, the needle 106 and its attached ferrule 96 are guided through the cuff receiving area 58 and the tissue bite area 60. The needle 106 and the ferrule 96 then enter the ferrule receiving aperture 102, and the ferrule 96 passes by the latch 110. Notice here, in FIG. 5F, that the needle end 112 is sloped in this orientation, thereby allowing the latch 110 to push down against the needle 106 and interfere with the edge of the suture ferrule 96. Accordingly, when the needle 106 is withdrawn this time, as illustrated in FIG. 5G, the latch 110 pushes the ferrule 96 off of the needle end 112, leaving the suture ferrule 96 behind in the ferrule receiving aperture 102. As shown in FIG. 5G, the needle 106 has been retracted by the actuator along a direction 118 parallel to the longitudinal axis of the needle 106 away from the distal end 70 of the guide tip 54. The end 112 of the needle 106 (and usually the needle 106 with it) starts out oriented as shown in FIG. 5F, but rotates ninety degrees during the retraction in order to present the non-sloped side of the needle 106 so the ferrule 96 can be picked up on the subsequent engagement. The needle 106, as illustrated in FIG. 5G, depicts the needle 106 after rotation.

As shown in the partial cross-sectional view of FIG. 5H, a sewing cuff 120 of replacement heart valve 122 is placed into the cuff receiving area 58. It should be noted that the term "sewing cuff" may also include, but is not limited to a sewing ring or suturing ring. The sewing cuff 120 can be any material through which suture may be passed or sewn in order to ultimately hold the replacement anatomical structure in position for the structure it is replacing. As shown in FIG. 5I-1, the needle 106 has been advanced by an actuator along a direction 116 parallel to a longitudinal axis of the needle 106 towards the distal end 70 of the guide tip 54. Along the way, the needle 106 is guided through the cuff receiving area 58 and the tissue bite area 60. Since there is a sewing cuff 120 in the cuff receiving area 58, the needle 106 passes through the sewing cuff 120. The needle 106 then enters the ferrule receiving aperture 102, passes by the latch 110, and couples to the ferrule 96.

In this embodiment, as discussed previously with regard to FIGS. 3A and 3B, and as shown more clearly in the enlarged view of FIG. 5I-2, the needle 106 is guided in part by a transition needle guide 66 between the cuff receiving area 58 and the tissue bite area 60. Depending on the properties of the sewing cuff 120, the cuff 120 may tend to be pushed by the needle 106 into the transition needle guide 66 as the needle 106 is advanced through the sewing cuff 120. Therefore, in some embodiments, it may be advantageous for the transition needle guide 66 to have a flared end 124 facing the cuff receiving area 58. As shown in FIG. 5I-2, the flared end 124 can accommodate a portion 126 of the sewing cuff 120 pushed into the flared end 124 without jamming the needle 106 in the transition needle guide 66.

Next, as shown in FIG. 5J, the needle 106 has been retracted by the actuator along a direction 118 parallel to the longitudinal axis of the needle 106 away from the distal end 70 of the guide tip 54. The end 112 of the needle 106 starts out oriented as shown in FIG. 5I-1 and is configured in that orientation to provide no edge for the latch 110 to grab the ferrule 96, thereby enabling the needle 106 to withdraw the ferrule 96 (and the suture 84 attached to the ferrule 96) back through the tissue bite area 60, back through the transition guide 66 with the flared end 124, back through the sewing cuff 120, and back into the needle guide 62 as shown in FIG. 5J. The suture 84 is free to pass through the suture removal passage 72, and the stitched replacement valve 122 can be lifted out of the cuff receiving area 58 as illustrated in FIG. 5K. Depending on the embodiment, the ferrule 96 can be removed from the needle 106 in the position of FIG. 5K by backing the needle 106 even further away from the distal end 70, causing an edge of the ferrule 96 to be pushed off of the needle 106 by a ferrule release spring 128 which is biased to ride against the needle 106. Such ferrule release features are known to those skilled in the art, for example, as taught in U.S. Pat. No. 8,398,657 to Sauer, entitled, "Multi-Fire Suturing Instrument with Proximal Ferrule Release Feature", the entirety of which is hereby incorporated by reference.

Before illustrating and describing an embodiment of how the replacement valve installation could be completed, it is helpful to remember that embodiments of the surgical suturing device described herein have a guide tip 54 defining a cuff receiving area 58 and a tissue bite area 60. The guide tip 54 also has at least one needle guide 62 and/or 66 configured to guide at least one needle 106 through the cuff receiving area 58 and the tissue bite area 60. For ease of explanation, the partial cross-sectional views of FIGS. 5A-5K illustrate the operation of a single needle 106. However, embodiments with one or more needles are contemplated and intended to be covered by the scope of the claims herein. Although any number of needles are contemplated, there is an efficiency advantage for embodiments which utilize one or more pairs of needles. In such embodiments, each pair of needles can be used to manipulate both ends of a single suture. As an example, consider the scenario illustrated in FIGS. 6A-6K.

Figure 6A:
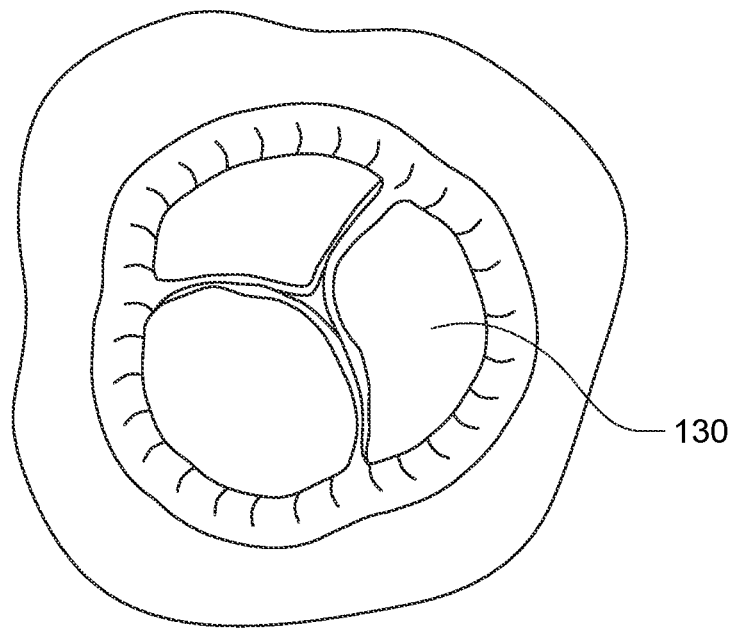
FIG. 6A schematically illustrates a heart valve in need of replacement.
Figure 6B:
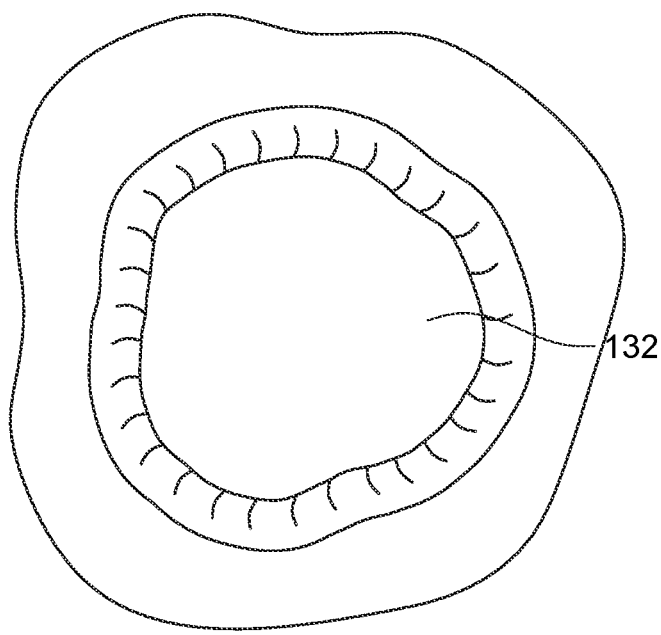
FIG. 6B schematically illustrates the heart valve of FIG. 6A with the valve leaflets removed and the valve annulus remaining in preparation for installation of a replacement heart valve.
Figure 6C:
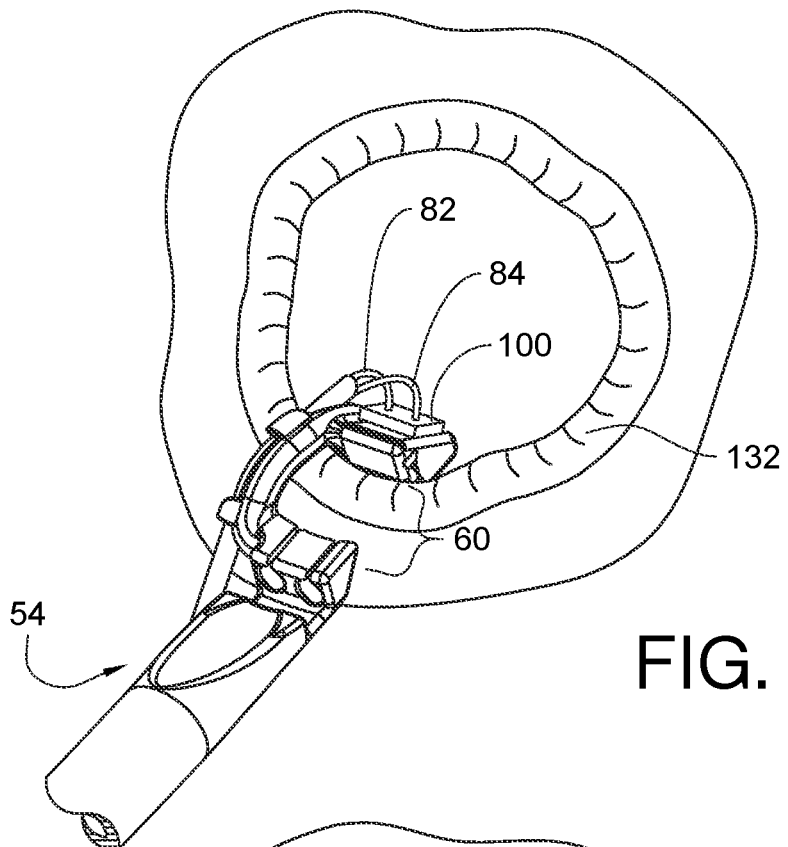
FIG. 6C illustrates the placement of a tissue bite area of one embodiment of a surgical suturing device guide tip over the annulus where a replacement heart valve will be installed.

FIG. 6A schematically illustrates a diseased heart valve 130 in need of replacement. As a first action, a surgeon might gain access to the diseased valve 130 and dissect the leaflets of the valve, leaving the valve annulus 132 in preparation for installation of a replacement heart valve as shown in FIG. 6B. In this example, it would be desirable to attach the replacement heart valve to the remaining annulus 132. Therefore, as illustrated in FIG. 6C, the tissue bite area 60 of a surgical suturing device could be placed over a portion of the annulus 132 where it would be desired to make some attachment stitches. In this embodiment, the guide tip 54 has a suture delivery tube 82 holding the middle portion of a suture 84. A pledget 100 is pre-threaded on the suture 84 and each end of the suture has its own ferrule (not visible in this view). Each ferrule is loaded into its own ferrule receiving aperture, and each ferrule receiving aperture has a corresponding needle. Although the needles and ferrules are not visible in this view, the operation of each needle/ferrule pair would work as previously described for the examples of FIGS. 5A-5K.

Figure 6D:
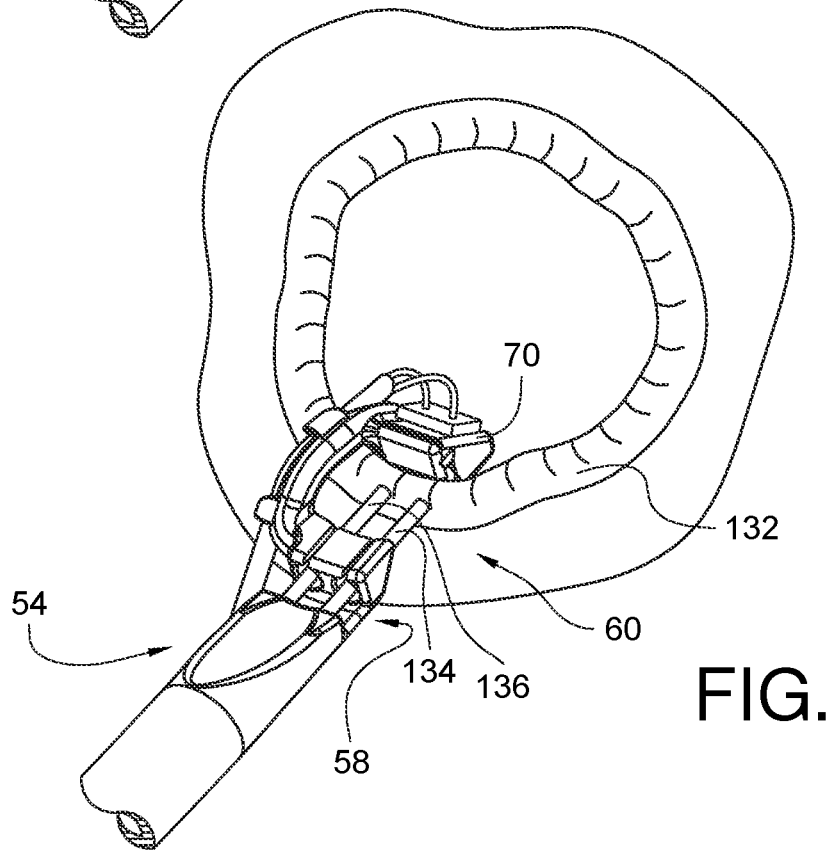
FIG. 6D illustrates the advancement of two needles of the surgical suturing device of FIG. 6C through the tissue in the tissue bite area.
Figure 6E:
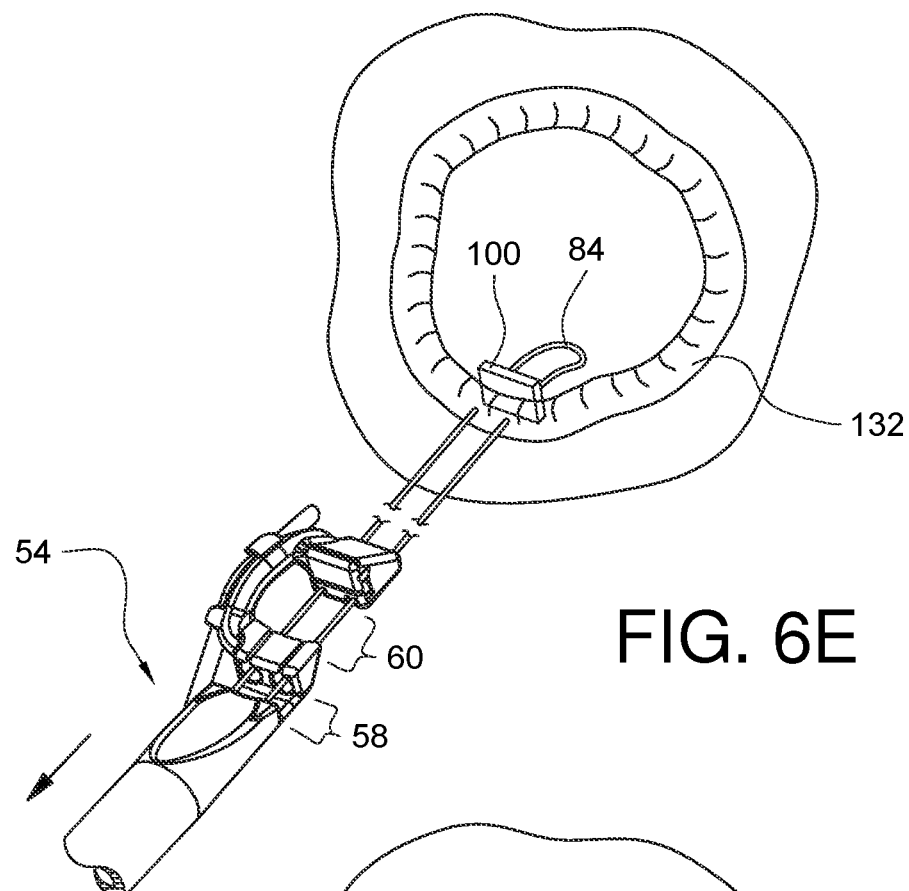
FIG. 6E illustrates the drawing back of two ends of a suture, through the annulus tissue in the tissue bite area, as well as the partial positioning of a pledget pre-installed on the suture.

As illustrated in FIG. 6D, the first and second needles 134, 136 can be advanced through the annulus 132 in the tissue bite area 60. The needles 134, 136 may be advanced simultaneously or at different times. A single actuator may advantageously control the movement of both needles 134, 136, or each needle 134, 136 may have its own actuator. The needles 134, 136 couple with their respective ferrules as described above, and then both ends of the suture 84 are drawn back through the annulus 132 in the tissue bite area 60, back through the cuff receiving area 58, and into the guide tip 54. The guide tip 54 can be removed from the annulus as illustrated in FIG. 6E, and the device can be pulled back to tighten the suture 84 against the pledget 100 and ultimately against the annulus 132.

Figure 6F:
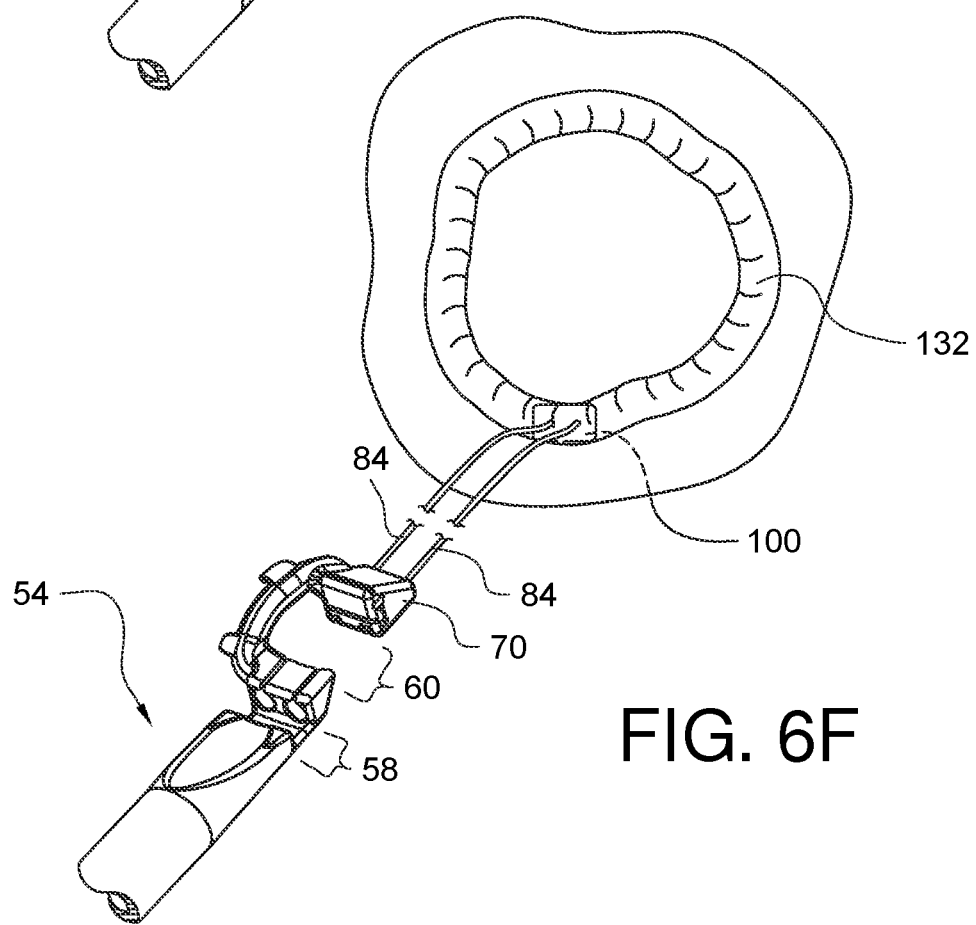
FIG. 6F illustrates the pledget pulled into a position behind the annulus tissue by the suture ends which have been drawn out and returned to a distal end of the guide tip.
Figure 6G:
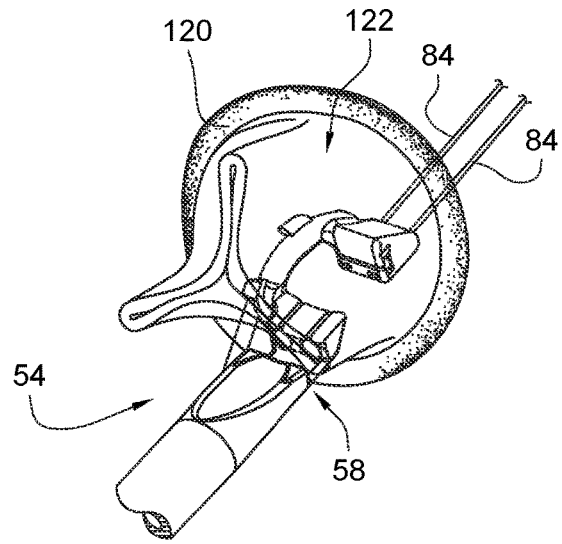
FIG. 6G illustrates one embodiment of a sewing cuff of a replacement heart valve being placed into a cuff receiving area of the surgical suturing device's guide tip.
Figure 6H:
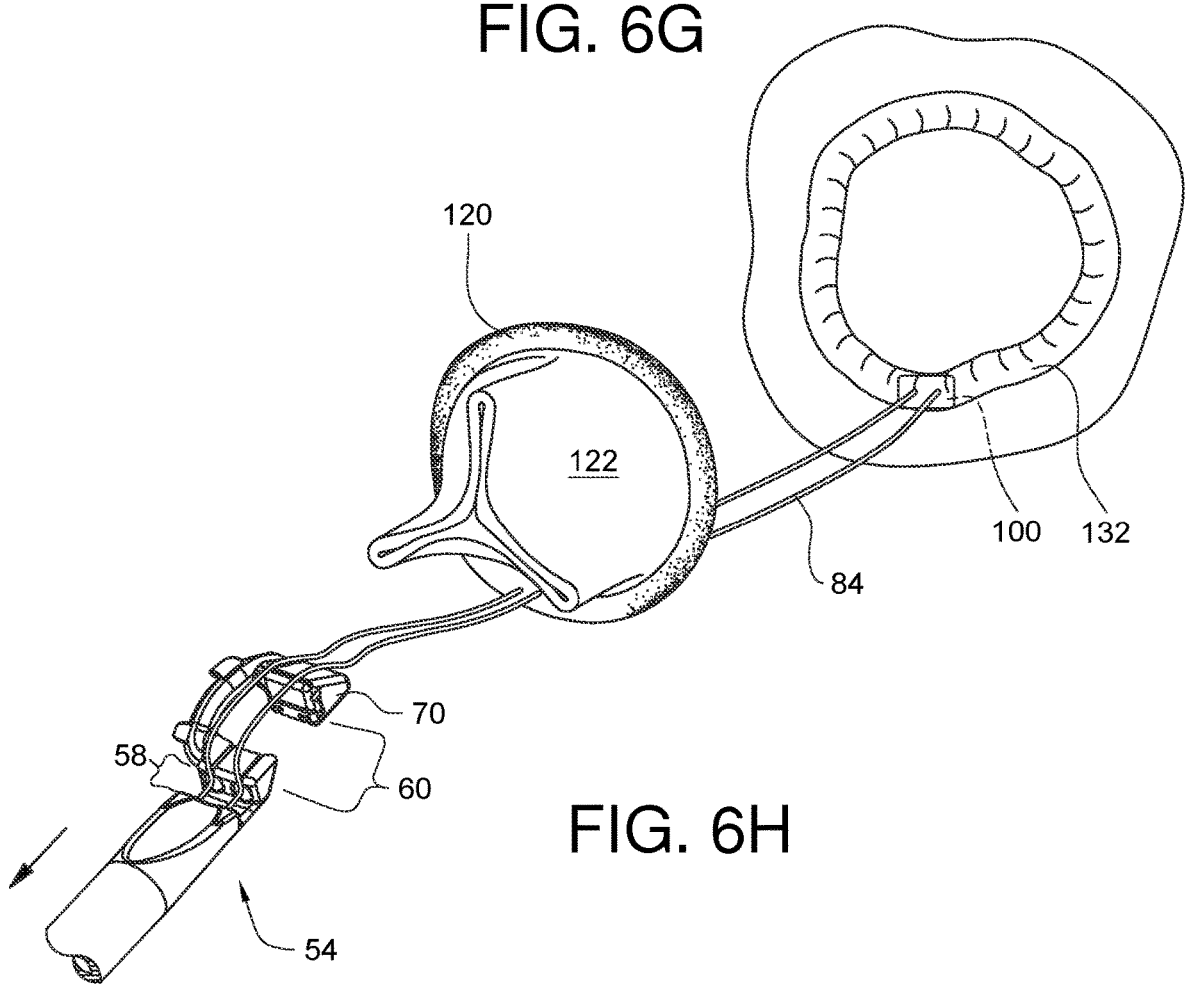
FIG. 6H illustrates an end result of drawing the two suture ends back through the sewing cuff of the replacement heart valve following a piercing of the sewing cuff by the two needles to retrieve ferrules coupled to the ends of the suture.

As the slack is removed from the suture 84 behind the pledget 100, the pledget 100 will move into a position on one side of the annulus 132 as illustrated in FIG. 6F. Preferably, but not necessarily, the spacing of the holes in the pledget 100 will be substantially the same as the spacing between the needles 134, 136. The ferrules coupled to the suture ends can be returned to the distal end 70 of the guide tip 54 as previously described, thereby resetting the device for the replacement valve. As illustrated in FIG. 6G, the sewing cuff 120 of a replacement valve 122 is then placed into the cuff receiving area 58 of the guide tip 54. The first and second needles can be advanced through the sewing cuff 120 in the cuff receiving area 58. Each needle extends into its respective ferrule receiving aperture, couples with its respective ferrule (as described above), and then both ends of the suture 84 are drawn back through the tissue bite area, through the sewing cuff 120 in the cuff receiving area 58, and into the guide tip 54. The replacement valve 122 can then be lifted out of the guide tip 54 as shown in FIG. 6H. By using a pair of needles as described, both ends of suture 84 can be placed simultaneously or at nearly the same time. Furthermore, the spacing between corresponding stitches of the annulus 132 and the sewing cuff 120 are consistent due to the substantially consistent spacing between the two needles in the pair. This may help the replacement anatomical structure to align better with the tissue to which it attaches. Additionally, the surgical suturing device described herein may offer a more reliable tissue bite, potentially leading to stronger and more reliable suture stitches. With more reliable stitches, there is a potential to reduce the number of sutures per replacement valve. For example, in the case of an aortic valve replacement, twenty or more sutures are often needed to ensure the valve is securely attached. A reduction in that number of sutures would be a welcome savings in time, effort, and materials.

Figure 6I:
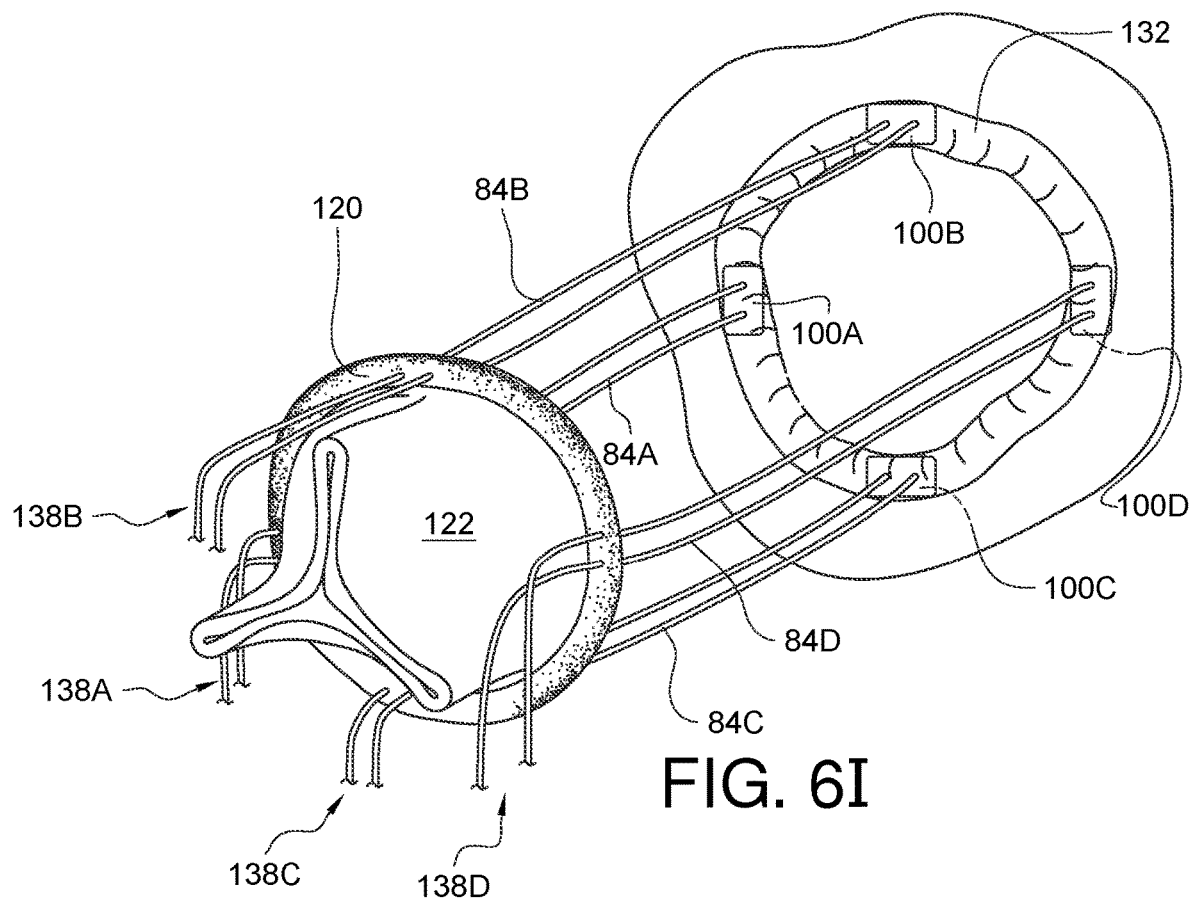
FIG. 6I illustrates several sets of suture ends placed through annulus tissue and corresponding points in the sewing cuff of the replacement heart valve.

The ferrules on the ends of the suture can be released, for example, as described above. Another suture can be loaded into the device, and the process can be repeated around the annulus 132 as many times as desired by the surgeon. As a simple example, FIG. 6I illustrates the result of having performed the process four times with a two-needle device. Four sutures 84A, 84B, 84C, 84D have been placed in desired locations through the annulus 132 and through corresponding locations in the sewing cuff 120. Each suture 84A, 84B, 84C, 84D passes through both the annulus 132 and the sewing cuff 120 twice and is positioned so that it holds a respective pledget 100A, 100B, 100C, 100D against the annulus 132 and terminates in a respective pair of suture ends 138A, 138B, 138C, 138D. In practice, this process can be used for any number of sutures. The four sutures illustrated here are just for the convenience of explanation.

Figure 6J:
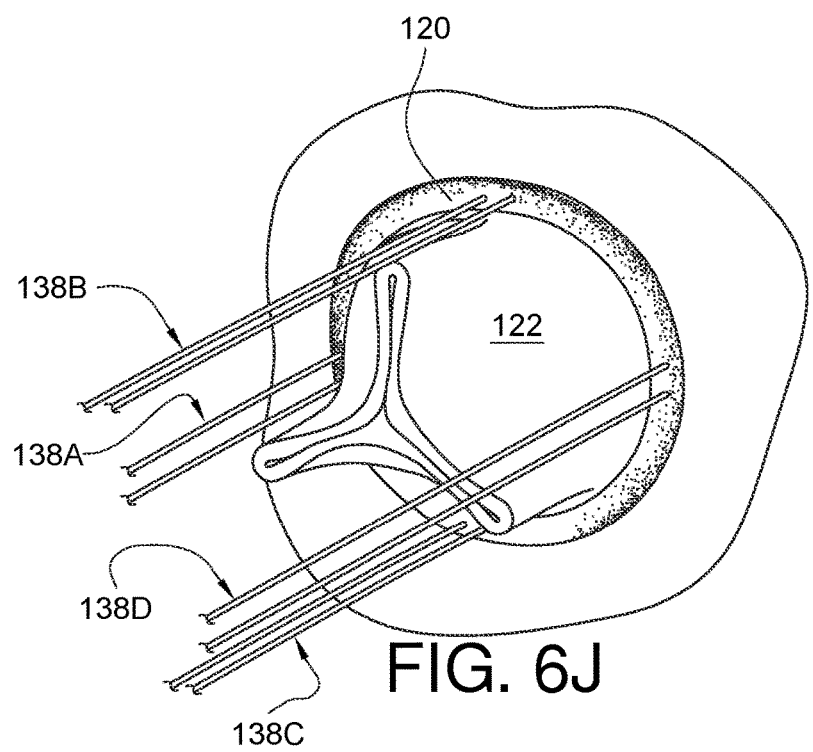
FIG. 6J illustrates tensioning the suture lines to remove slack in the sutures while the replacement valve is moved in place above the tissue annulus where the replacement valve is seated.
Figure 6K:
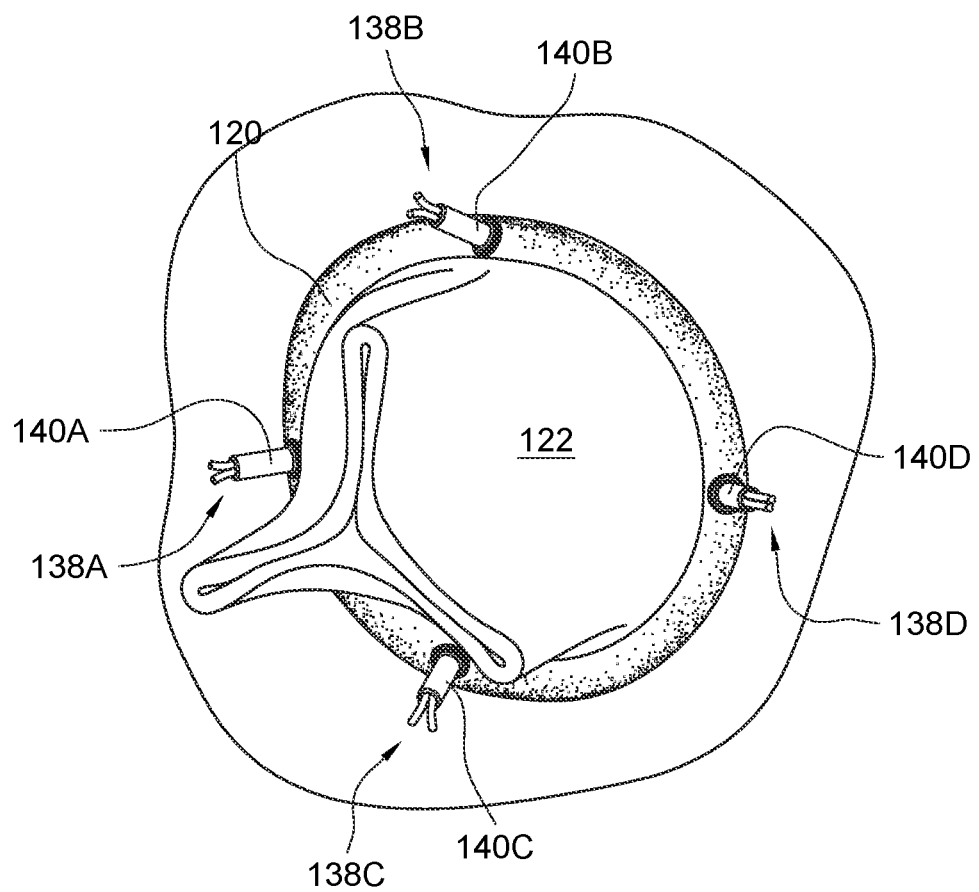
FIG. 6K illustrates one embodiment of knots holding the replacement valve against the tissue annulus.

As illustrated in FIG. 6J, tension can be maintained on the suture ends 138A, 138B, 138C, 138D while the replacement valve 122 is moved down the sutures and against the annulus. Each pair of suture ends 138A, 138B, 138C, 138D can then be tied off, knotted, clamped, or otherwise fixed against the sewing cuff 120 to hold the valve 122 in place. As one non-limiting example, each pair of suture ends 138A, 138B, 138C, 138D may be knotted with a mechanical knot 140A, 140B, 140C, 140D as illustrated in FIG. 6K. The mechanical knots 140A, 140B, 140C, 140D may be applied, for example, with a Ti-KNOT® device or a COR-KNOT® device available from LSI Solutions, Inc. of Victor, NY. (For example, find ordering contact information at www.lsisolutions.com). Other embodiments of mechanical knots or other types of knots may be used to finalize the attachment of the replacement anatomical structure.

Figure 7:
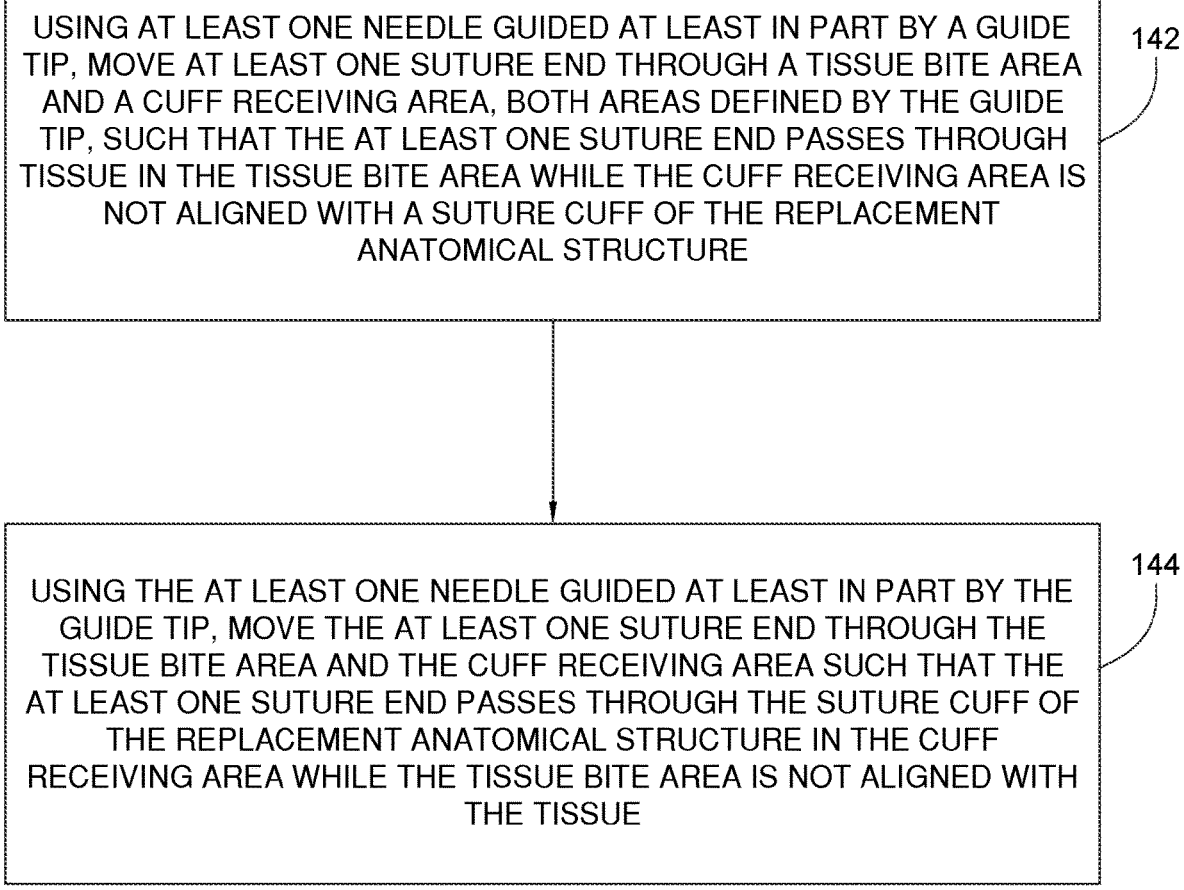

FIGS. 7 and 8 illustrate different embodiments of methods for installing a replacement anatomical structure. In the method embodiment of FIG. 7, in step 142, using at least one needle guided at least in part by a guide tip, at least one suture end is moved through a tissue bite area and a cuff receiving area, both areas defined by a guide tip, such that the at least one suture end passes through tissue in the tissue bite area while the cuff receiving area is not aligned with a suture cuff of the replacement anatomical structure. In step 144, using the at least one needle guided at least in part by the guide tip, the at least one suture end is moved through the tissue bite area and the cuff receiving area such that the at least one suture end passes through the suture cuff of the replacement anatomical structure in the cuff receiving area while the tissue bite area is not aligned with the tissue.

In the method embodiment of FIG. 8, in step 146, using first and second needles guided in part by a guide tip, the needles each having a ferrule engaging end removably coupled to respective first and second ferrules on respective first and second ends of a suture, the first and second suture ends are moved through a tissue bite area and a cuff receiving area, both areas defined by a guide tip, such that the first and second suture ends pass through tissue in the tissue bite area while the cuff receiving area is not aligned with a suture cuff of the replacement anatomical structure. In step 148, using the first and second needles, the first and second suture ends are moved through the tissue bite area and the cuff receiving area such that the first and second suture ends pass through the suture cuff of the replacement anatomical structure in the cuff receiving area while the tissue bite area is not aligned with the tissue.

In alternate embodiments, the suture could be passed through the sewing cuff in the cuff receiving area while there is also tissue in the tissue bite area and visa versa. Also, depending on the embodiment, it is not necessarily a limitation that the passing of the suture through the sewing cuff and then through the tissue (or visa versa) have to happen on different strokes of the needle. For example, the surgeon could align the tissue in the tissue bite area and the sewing cuff in the cuff receiving area during the same needle pass from a retracted position to the distal tip and then back. By doing this, the suture ends would be drawn through both the tissue and the sewing cuff in one retraction or movement of the needle.

Various advantages of a surgical suturing device for a replacement anatomical structure and methods for its use have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A suturing device comprising:
a housing;
an actuator coupled to a first portion of the housing such that the actuator is displaceable between a first actuator position and a second actuator position;
a shaft extending from a proximal end to a distal end along a shaft axis, wherein the shaft defines an interior portion that extends from the proximal end of the shaft to the distal end of the shaft, and wherein the proximal end of the shaft is coupled to a second portion of the housing;
a needle extending from a proximal end to a distal end along a longitudinal axis that is parallel to or coaxially aligned with the shaft axis, wherein the proximal end of the needle is coupled to a portion of the actuator and at least a portion of the needle extends through the interior portion of the shaft, wherein as the actuator is displaced from the first actuator position to the second actuator position, the distal end of the needle is displaced along the longitudinal axis from a first needle position to a second needle position, and wherein as the actuator is displaced from the second actuator position to the first actuator position, the distal end of the needle is displaced along the longitudinal axis from the second needle position to the first needle position; and
a guide tip coupled to the distal end of the shaft, the guide tip comprising:
a proximal portion;
a transition portion coupled to the proximal portion, wherein a transition passage extends through the transition portion from a proximal end of the transition portion to a distal end of the transition portion;
a distal portion coupled to the transition portion, the distal portion having a first ferrule receiving passage, wherein a first ferrule receiving aperture is disposed at a proximal end of the first ferrule receiving passage, and wherein at least a portion of the first ferrule receiving passage is configured to hold a first ferrule secured to a first portion of suture;
a first slot defined between a distal end of the proximal portion and the proximal end of the transition portion, the first slot defining a cuff receiving area configured to receive a portion of a first material; and
a second slot defined between the distal end of the transition portion and a proximal end of the distal portion, the second slot defining a tissue bite area configured to receive a portion of second material,
wherein in the first needle position, the distal end of the needle is disposed proximal to the distal end of the proximal portion and in the second needle position, the distal end of the needle is disposed adjacent to the first ferrule receiving aperture of the distal portion such that the distal end of the needle is configured to operatively engage the first ferrule secured to the first portion of suture, and
wherein as the needle displaces from the first needle position to the second needle position, the distal end of the needle displaces through a portion of the cuff receiving area, the transition passage, a portion of the tissue bite area, and a proximal portion of the first ferrule receiving passage, and as the needle displaces from the second needle position to the first needle position, the distal end of the needle is configured to retain the first ferrule secured to the first portion of suture as the distal end of the needle displaces through the proximal portion of the first ferrule receiving passage, the portion of the tissue bite area, the transition passage, and the portion of the cuff receiving area, and
wherein a first longitudinal distance between the distal end of the proximal portion and the proximal end of the transition portion is less than a second longitudinal distance between the distal end of the transition portion and the proximal end of the distal portion.

2. The suturing device of claim 1, wherein the distal portion of the guide tip includes a latch slot, wherein an end portion of the latch slot opens to the first ferrule receiving passage and the end portion of the latch slot is adjacent to the portion of the first ferrule receiving passage configured to hold the first ferrule secured to the first portion of suture, and
the guide tip further comprising a latch disposed at least partially in the latch slot, wherein an end portion of the latch is configured to contact an end portion of the first ferrule secured to the first portion of suture to prevent the first ferrule from displacing proximally relative to the first ferrule receiving passage as the distal end of the needle is displaced from the second needle position to the first needle position.

3. The suturing device of claim 1, wherein as the actuator is displaced from the first actuator position to the second actuator position, the distal end of the needle is displaced distally from the first needle position to the second needle position, and wherein as the actuator is displaced from the second actuator position to the first actuator position, the distal end of the needle is displaced proximally from the second needle position to the first needle position, and as the distal end of the needle is displaced proximally from the second needle position to the first needle position, the needle rotates 90 degrees about the longitudinal axis.

4. The suturing device of claim 1, wherein as the distal end of the needle is displaced from the second needle position to the first needle position, the needle rotates about the longitudinal axis.

5. The suturing device of claim 1, wherein in the second needle position, the distal end of the needle is disposed at or adjacent to the distal end of the distal portion of the guide tip.

6. The suturing device of claim 1, wherein the transition passage extends through the transition portion of the guide tip from the proximal end of the transition portion to the distal end of the transition portion along the longitudinal axis, and the first ferrule receiving passage extends from a proximal end to a distal end along the longitudinal axis.

7. The suturing device of claim 1, wherein the a portion of the first slot is aligned with the longitudinal axis and a portion of the second slot is aligned with the longitudinal axis.

8. The suturing device of claim 1, wherein a portion of the housing defines a grip portion, and wherein in the first actuator position, a lever portion of the actuator is in a first position relative to the grip portion of the housing and in the second actuator position, the lever portion of the actuator is in a second position relative to the grip portion of the housing.

9. The suturing device of claim 1, wherein the distal end of the needle is displaced linearly from the first needle position to the second needle position.

10. The suturing device of claim 1, wherein the actuator is pivotably coupled to the first portion of the housing such that the actuator is pivotably displaceable between the first actuator position and the second actuator position.

11. The suturing device of claim 1, wherein the portion of the first ferrule receiving passage configured to hold the first ferrule secured to the first portion of suture is disposed distally to the proximal portion of the first ferrule receiving passage.

12. The suturing device of claim 1, further comprising:
a second needle extending from a proximal end to a distal end along a second longitudinal axis that is parallel to the longitudinal axis, wherein the proximal end of the second needle is coupled to a second portion of the actuator and at least a portion of the second needle extends through the interior portion of the shaft, wherein as the actuator is displaced from the first actuator position to the second actuator position, the distal end of the second needle is displaced along the second longitudinal axis from a third needle position to a fourth needle position, and wherein as the actuator is displaced from the second actuator position to the first actuator position, the distal end of the second needle is displaced along the second longitudinal axis from the fourth needle position to the third needle position.

13. The suturing device of claim 1, wherein the proximal portion of the guide tip is coupled to the transition portion of the guide tip by a cuff support that extends parallel to the longitudinal axis from the distal end of the proximal portion to the proximal end of the transition portion, wherein a surface of the cuff support at least partially defines the first slot.

14. The suturing device of claim 13, wherein the distal portion of the guide tip is coupled to the transition portion of the guide tip by a connector portion, the connector portion extending from a lateral end of the distal portion to a lateral end of the transition portion.

15. The suturing device of claim 14, wherein the actuator is pivotably coupled to the first portion of the housing about a pivot axis that is normal to the shaft axis, and wherein a first plane is normal to the pivot axis and includes the shaft axis, and a second plane that includes the shaft axis and is normal to the shaft axis, and wherein the connector portion is disposed on a first side of the second plane and the cuff support is disposed on a second side of the second plane.

16. The suturing device of claim 15, wherein the connector portion is disposed on a first side of the first plane, and the first plane bisects the cuff support.

17. A method of assembling a suturing device, the method comprising:
coupling an actuator to a first portion of a housing such that the actuator is displaceable between a first actuator position and a second actuator position;
coupling a proximal end of a shaft to a second portion of the housing, wherein the shaft extends from the proximal end to a distal end along a shaft axis, and wherein the shaft defines an interior portion that extends from the proximal end of the shaft to the distal end of the shaft;
coupling a proximal end of a needle to a portion of the actuator such that at least a portion of the needle extends through the interior portion of the shaft, the needle extending from the proximal end to a distal end along a longitudinal axis that is parallel to or coaxially aligned with the shaft axis, wherein as the actuator is displaced from the first actuator position to the second actuator position, the distal end of the needle is displaced along the longitudinal axis from a first needle position to a second needle position, and wherein as the actuator is displaced from the second actuator position to the first actuator position, the distal end of the needle is displaced along the longitudinal axis from the second needle position to the first needle position; and
coupling a guide tip to the distal end of the shaft, the guide tip comprising:
a proximal portion;
a transition portion coupled to the proximal portion, wherein a transition passage extends through the transition portion from a proximal end of the transition portion to a distal end of the transition portion;
a distal portion coupled to the transition portion, the distal portion having a first ferrule receiving passage, wherein a first ferrule receiving aperture is disposed at a proximal end of the first ferrule receiving passage, wherein at least a portion of the first ferrule receiving passage is configured to hold a first ferrule secured to a first portion of suture;
a first slot defined between a distal end of the proximal portion and the proximal end of the transition portion, the first slot defining a cuff receiving area configured to receive a portion of a first material; and
a second slot defined between the distal end of the transition portion and a proximal end of the distal portion, the second slot defining a tissue bite area configured to receive a portion of second material,
wherein in the first needle position, the distal end of the needle is disposed proximal to the distal end of the proximal portion and in the second needle position, the distal end of the needle is disposed adjacent to the first ferrule receiving aperture of the distal portion such that the distal end of the needle is configured to operatively engage the first ferrule secured to the first portion of suture, and
wherein as the needle displaces from the first needle position to the second needle position, the distal end of the needle displaces through a portion of the cuff receiving area, the transition passage, a portion of the tissue bite area, and a proximal portion of the first ferrule receiving passage, and
as the needle displaces from the second needle position to the first needle position, the distal end of the needle is configured to retain the first ferrule secured to the first portion of suture as the distal end of the needle displaces through the proximal portion of the first ferrule receiving passage, the portion of the tissue bite area, the transition passage, and the portion of the cuff receiving area, and
wherein a first longitudinal distance between the distal end of the proximal portion and the proximal end of the transition portion is less than a second longitudinal distance between the distal end of the transition portion and the proximal end of the distal portion.

18. A suturing device comprising:
a housing;
an actuator coupled to a first portion of the housing such that the actuator is displaceable between a first actuator position and a second actuator position;
a shaft extending from a proximal end to a distal end along a shaft axis, wherein the shaft defines an interior portion that extends from the proximal end of the shaft to the distal end of the shaft, and wherein the proximal end of the shaft is coupled to a second portion of the housing;

a needle extending from a proximal end to a distal end along a longitudinal axis that is parallel to or coaxially aligned with the shaft axis, wherein the proximal end of the needle is coupled to a portion of the actuator and at least a portion of the needle extends through the interior portion of the shaft, wherein as the actuator is displaced from the first actuator position to the second actuator position, the distal end of the needle is displaced along the longitudinal axis from a first needle position to a second needle position, and wherein as the actuator is displaced from the second actuator position to the first actuator position, the distal end of the needle is displaced along the longitudinal axis from the second needle position to the first needle position; and a guide tip coupled to the distal end of the shaft, the guide tip comprising:

a proximal portion;

a transition portion coupled to the proximal portion, wherein a transition passage extends through the transition portion from a proximal end of the transition portion to a distal end of the transition portion;

a distal portion coupled to the transition portion, the distal portion having a first ferrule receiving passage, wherein a first ferrule receiving aperture is disposed at a proximal end of the first ferrule receiving passage, and wherein at least a portion of the first ferrule receiving passage is configured to hold a first ferrule secured to a first portion of suture;

a first slot defined between a distal end of the proximal portion and the proximal end of the transition portion, the first slot defining a cuff receiving area configured to receive a portion of a first material; and a second slot defined between the distal end of the transition portion and a proximal end of the distal portion, the second slot defining a tissue bite area configured to receive a portion of second material, wherein in the first needle position, the distal end of the needle is disposed proximal to the distal end of the proximal portion and in the second needle position, the distal end of the needle is disposed adjacent to the first ferrule receiving aperture of the distal portion such that the distal end of the needle is configured to operatively engage the first ferrule secured to the first portion of suture, and wherein as the needle displaces from the first needle position to the second needle position, the distal end of the needle displaces through a portion of the cuff receiving area, the transition passage, a portion of the tissue bite area, and a proximal portion of the first ferrule receiving passage, and as the needle displaces from the second needle position to the first needle position, the distal end of the needle is configured to retain the first ferrule secured to the first portion of suture as the distal end of the needle displaces through the proximal portion of the first ferrule receiving passage, the portion of the tissue bite area, the transition passage, and the portion of the cuff receiving area, and wherein as the actuator is displaced from the first actuator position to the second actuator position, the distal end of the needle is displaced distally from the first needle position to the second needle position, and wherein as the actuator is displaced from the second actuator position to the first actuator position, the distal end of the needle is displaced proximally from the second needle position to the first needle position, and as the distal end of the needle is displaced proximally from the second needle position to the first needle position, the needle rotates 90 degrees about the longitudinal axis.

19. A suturing device comprising:

a housing;

an actuator coupled to a first portion of the housing such that the actuator is displaceable between a first actuator position and a second actuator position;

a shaft extending from a proximal end to a distal end along a shaft axis, wherein the shaft defines an interior portion that extends from the proximal end of the shaft to the distal end of the shaft, and wherein the proximal end of the shaft is coupled to a second portion of the housing;

a needle extending from a proximal end to a distal end along a longitudinal axis that is parallel to or coaxially aligned with the shaft axis, wherein the proximal end of the needle is coupled to a portion of the actuator and at least a portion of the needle extends through the interior portion of the shaft, wherein as the actuator is displaced from the first actuator position to the second actuator position, the distal end of the needle is displaced along the longitudinal axis from a first needle position to a second needle position, and wherein as the actuator is displaced from the second actuator position to the first actuator position, the distal end of the needle is displaced along the longitudinal axis from the second needle position to the first needle position; and a guide tip coupled to the distal end of the shaft, the guide tip comprising:

a proximal portion;

a transition portion coupled to the proximal portion, wherein a transition passage extends through the transition portion from a proximal end of the transition portion to a distal end of the transition portion;

a distal portion coupled to the transition portion, the distal portion having a first ferrule receiving passage, wherein a first ferrule receiving aperture is disposed at a proximal end of the first ferrule receiving passage, and wherein at least a portion of the first ferrule receiving passage is configured to hold a first ferrule secured to a first portion of suture;

a first slot defined between a distal end of the proximal portion and the proximal end of the transition portion, the first slot defining a cuff receiving area configured to receive a portion of a first material; and a second slot defined between the distal end of the transition portion and a proximal end of the distal portion, the second slot defining a tissue bite area configured to receive a portion of second material, wherein in the first needle position, the distal end of the needle is disposed proximal to the distal end of the proximal portion and in the second needle position, the distal end of the needle is disposed adjacent to the first ferrule receiving aperture of the distal portion such that the distal end of the needle is configured to operatively engage the first ferrule secured to the first portion of suture, and wherein as the needle displaces from the first needle position to the second needle position, the distal end of the needle displaces through a portion of the cuff receiving area, the transition passage, a portion of the tissue bite area, and a proximal portion of the first ferrule receiving passage, and as the needle displaces from the second needle position to the first needle position, the distal end of the needle is configured to retain the first ferrule secured to the first portion of suture as the distal end of the needle displaces through the proximal portion of the first ferrule receiving passage, the portion of the tissue bite area, the transition passage, and the portion of the cuff receiving area, and wherein as the distal end of the needle is displaced from the second needle position to the first needle position, the needle rotates about the longitudinal axis.

20. A suturing device comprising:

a housing;

an actuator coupled to a first portion of the housing such that the actuator is displaceable between a first actuator position and a second actuator position;

a shaft extending from a proximal end to a distal end along a shaft axis, wherein the shaft defines an interior portion that extends from the proximal end of the shaft to the distal end of the shaft, and wherein the proximal end of the shaft is coupled to a second portion of the housing;

a needle extending from a proximal end to a distal end along a longitudinal axis that is parallel to or coaxially aligned with the shaft axis, wherein the proximal end of the needle is coupled to a portion of the actuator and at least a portion of the needle extends through the interior portion of the shaft, wherein as the actuator is displaced from the first actuator position to the second actuator position, the distal end of the needle is displaced along the longitudinal axis from a first needle position to a second needle position, and wherein as the actuator is displaced from the second actuator position to the first actuator position, the distal end of the needle is displaced along the longitudinal axis from the second needle position to the first needle position; and a guide tip coupled to the distal end of the shaft, the guide tip comprising:
 a proximal portion;
 a transition portion coupled to the proximal portion, wherein a transition passage extends through the transition portion from a proximal end of the transition portion to a distal end of the transition portion;
 a distal portion coupled to the transition portion, the distal portion having a first ferrule receiving passage, wherein a first ferrule receiving aperture is disposed at a proximal end of the first ferrule receiving passage, and wherein at least a portion of the first ferrule receiving passage is configured to hold a first ferrule secured to a first portion of suture;
 a first slot defined between a distal end of the proximal portion and the proximal end of the transition portion, the first slot defining a cuff receiving area configured to receive a portion of a first material; and
 a second slot defined between the distal end of the transition portion and a proximal end of the distal portion, the second slot defining a tissue bite area configured to receive a portion of second material,
 wherein in the first needle position, the distal end of the needle is disposed proximal to the distal end of the proximal portion and in the second needle position, the distal end of the needle is disposed adjacent to the first ferrule receiving aperture of the distal portion such that the distal end of the needle is configured to operatively engage the first ferrule secured to the first portion of suture, and
 wherein as the needle displaces from the first needle position to the second needle position, the distal end of the needle displaces through a portion of the cuff receiving area, the transition passage, a portion of the tissue bite area, and a proximal portion of the first ferrule receiving passage, and
 as the needle displaces from the second needle position to the first needle position, the distal end of the needle is configured to retain the first ferrule secured to the first portion of suture as the distal end of the needle displaces through the proximal portion of the first ferrule receiving passage, the portion of the tissue bite area, the transition passage, and the portion of the cuff receiving area,
 wherein the proximal portion of the guide tip is coupled to the transition portion of the guide tip by a cuff support that extends parallel to the longitudinal axis from the distal end of the proximal portion to the proximal end of the transition portion, wherein a surface of the cuff support at least partially defines the first slot,
 wherein the distal portion of the guide tip is coupled to the transition portion of the guide tip by a connector portion, the connector portion extending from a lateral end of the distal portion to a lateral end of the transition portion, and
 wherein the actuator is pivotably coupled to the first portion of the housing about a pivot axis that is normal to the shaft axis, and wherein a first plane is normal to the pivot axis and includes the shaft axis, and a second plane that includes the shaft axis and is normal to the shaft axis, and wherein the connector portion is disposed on a first side of the second plane and the cuff support is disposed on a second side of the second plane.

21. A suturing device comprising:

a housing;

an actuator coupled to a first portion of the housing such that the actuator is displaceable between a first actuator position and a second actuator position;

a shaft extending from a proximal end to a distal end along a shaft axis, wherein the shaft defines an interior portion that extends from the proximal end of the shaft to the distal end of the shaft, and wherein the proximal end of the shaft is coupled to a second portion of the housing;

a needle extending from a proximal end to a distal end along a longitudinal axis that is parallel to or coaxially aligned with the shaft axis, wherein the proximal end of the needle is coupled to a portion of the actuator and at least a portion of the needle extends through the interior portion of the shaft, wherein as the actuator is displaced from the first actuator position to the second actuator position, the distal end of the needle is displaced along the longitudinal axis from a first needle position to a second needle position, and wherein as the actuator is displaced from the second actuator position to the first actuator position, the distal end of the needle is displaced along the longitudinal axis from the second needle position to the first needle position; and a guide tip coupled to the distal end of the shaft, the guide tip comprising:
 a proximal portion;
 a transition portion coupled to the proximal portion, wherein a transition passage extends through the transition portion from a proximal end of the transition portion to a distal end of the transition portion;
 a distal portion coupled to the transition portion, the distal portion having a first ferrule receiving passage, wherein a first ferrule receiving aperture is disposed at a proximal end of the first ferrule receiving passage, and wherein at least a portion of the first ferrule receiving passage is configured to hold a first ferrule secured to a first portion of suture;

a first slot defined between a distal end of the proximal portion and the proximal end of the transition portion, the first slot defining a cuff receiving area configured to receive a portion of a first material; and a second slot defined between the distal end of the transition portion and a proximal end of the distal portion, the second slot defining a tissue bite area configured to receive a portion of second material, wherein in the first needle position, the distal end of the needle is disposed proximal to the distal end of the proximal portion and in the second needle position, the distal end of the needle is disposed adjacent to the first ferrule receiving aperture of the distal portion such that the distal end of the needle is configured to operatively engage the first ferrule secured to the first portion of suture, and wherein as the needle displaces from the first needle position to the second needle position, the distal end of the needle displaces through a portion of the cuff receiving area, the transition passage, a portion of the tissue bite area, and a proximal portion of the first ferrule receiving passage, and as the needle displaces from the second needle position to the first needle position, the distal end of the needle is configured to retain the first ferrule secured to the first portion of suture as the distal end of the needle displaces through the proximal portion of the first ferrule receiving passage, the portion of the tissue bite area, the transition passage, and the portion of the cuff receiving area, and wherein the distal portion of the guide tip includes a latch slot, wherein an end portion of the latch slot opens to the first ferrule receiving passage and the end portion of the latch slot is adjacent to the portion of the first ferrule receiving passage configured to hold the first ferrule secured to the first portion of suture, and the guide tip further comprising a latch disposed at least partially in the latch slot, wherein an end portion of the latch is configured to contact an end portion of the first ferrule secured to the first portion of suture to prevent the first ferrule from displacing proximally relative to the first ferrule receiving passage as the distal end of the needle is displaced from the second needle position to the first needle position.

* * * * *